US012362048B1

(12) United States Patent
Vaidya et al.

(10) Patent No.: US 12,362,048 B1
(45) Date of Patent: Jul. 15, 2025

(54) SYSTEMS AND METHODS FOR SIGNAL DIGITIZATION

(71) Applicant: Anumana, Inc., Cambridge, MA (US)

(72) Inventors: Suthirth Vaidya, Bengaluru (IN); Rakesh Barve, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/653,425

(22) Filed: May 2, 2024

(51) Int. Cl.
*G16H 10/60* (2018.01)
*G16H 30/20* (2018.01)
*G16H 30/40* (2018.01)

(52) U.S. Cl.
CPC .......... *G16H 10/60* (2018.01); *G16H 30/20* (2018.01); *G16H 30/40* (2018.01)

(58) Field of Classification Search
CPC ......... G16H 10/60; G16H 30/20; G16H 30/40
See application file for complete search history.

(56) References Cited

U.S. PATENT DOCUMENTS

| | | | | |
|---|---|---|---|---|
| 2017/0258336 | A1* | 9/2017 | Furness, III | ........... A61B 5/026 |
| 2019/0269344 | A1 | 9/2019 | Shah | |
| 2023/0016393 | A1* | 1/2023 | Boleyn | .................. A61B 5/361 |

FOREIGN PATENT DOCUMENTS

| | | | | |
|---|---|---|---|---|
| KR | 20230025965 A | * | 2/2023 | ........... A61B 5/7275 |
| TW | M328045 U | | 3/2008 | |
| WO | 2002101681 A1 | | 12/2002 | |
| WO | WO-2022070109 A1 | * | 4/2022 | ......... A61B 5/02427 |

* cited by examiner

*Primary Examiner* — Ross Varndell
(74) *Attorney, Agent, or Firm* — Caldwell Intellectual Property Law

(57) ABSTRACT

Described herein are systems and methods for signal digitization. A system may include a camera; a network interface device; a user interface; and a computing device configured to, using the camera, capture an image of a signal; determine a signal metric as a function of the image of the signal; and using the user interface, display the signal metric to a user; wherein the system is communicatively connected to a repository of deidentified patient health information.

14 Claims, 14 Drawing Sheets

SYSTEMS AND METHODS FOR SIGNAL DIGITIZATION

FIELD OF THE INVENTION

The present invention generally relates to the field of signal digitization. In particular, the present invention is directed to systems and methods for signal digitization.

BACKGROUND

Medical data such as electrocardiogram (ECG) data may be recorded or stored in a physical format such as on paper. Such data may also be traditionally analyzed manually by a specialist. In some situations, a device for recording medical data may be available, but use may be limited by availability of specialists trained to analyze output data.

SUMMARY OF THE DISCLOSURE

In an aspect, a system for signal digitization may include a camera; a network interface device; a user interface; and a computing device configured to, using the camera, capture an image of a signal; determine a signal metric as a function of the image of the signal; and using the user interface, display the signal metric to a user; wherein the system is communicatively connected to a repository of deidentified patient health information.

In another aspect, a method of signal digitization may include, using a camera and at least a processor, capturing an image of a signal; using the at least a processor, determining a signal metric as a function of the image of the signal; and using a user interface and the at least a processor, displaying the signal metric to a user; wherein the at least a processor is communicatively connected to a repository of deidentified patient health information.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for signal digitization. In some embodiments, a system may include a mobile device including a camera, a network interface device, a user interface, and a computing device. Such a mobile device may capture an image of a signal, such as without limitation a physical electrocardiogram (ECG) record. One or more processing steps may be performed on such image which may result in, as examples, a signal metric and/or an abnormality datum. Such a system may allow medical professionals to quickly and efficiently analyze signals without the need for manual analysis by a specialist.

Figure 1:
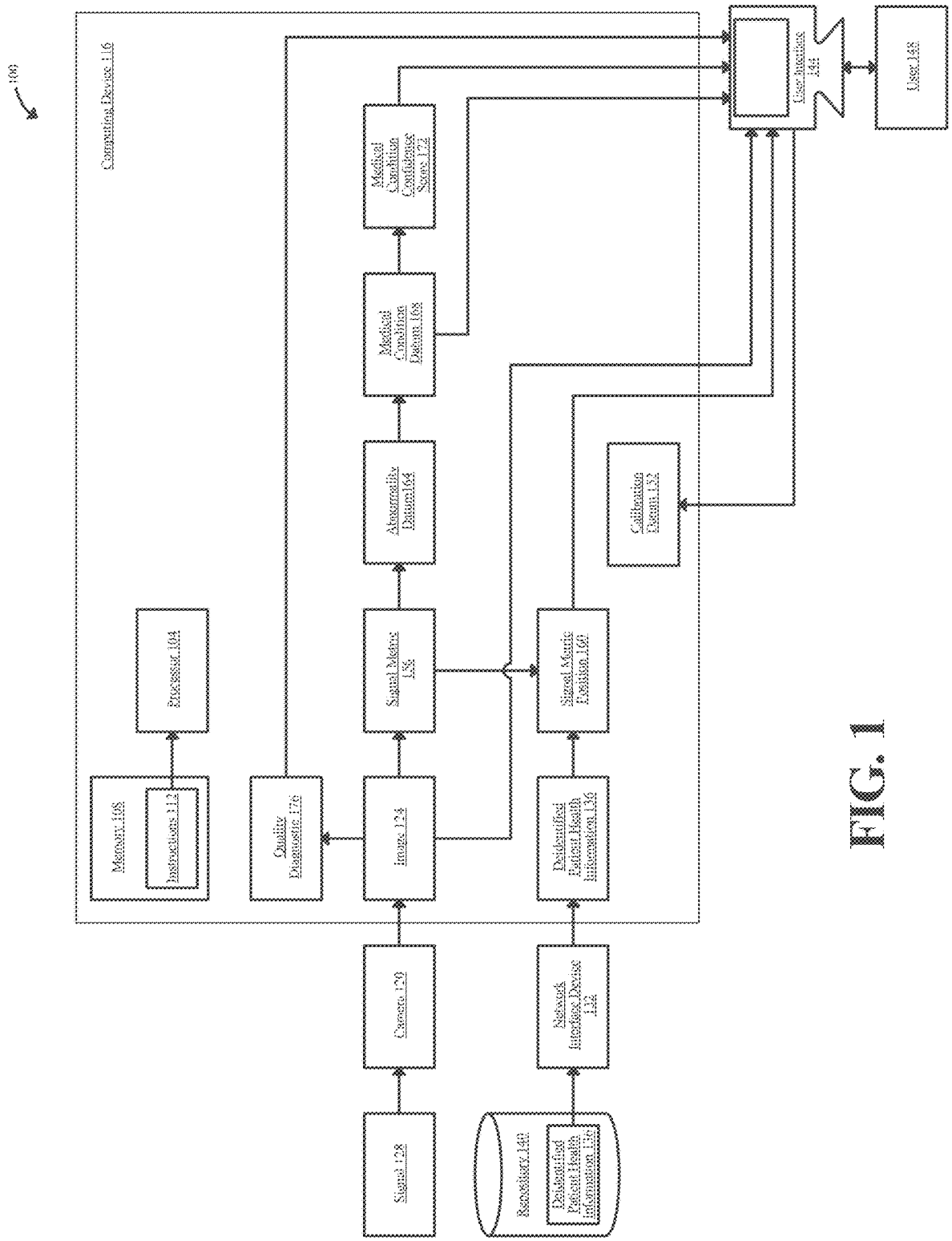
FIG. 1 is a diagram depicting an exemplary embodiment of a system for signal digitization.

Referring now to FIG. 1, an exemplary embodiment of a system 100 for signal digitization is illustrated. System 100 may include a computing device. System 100 may include a processor. Processor may include, without limitation, any processor described in this disclosure. Processor may be included in computing device. Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device.

Still referring to FIG. 1, in some embodiments, system 100 may include at least a processor 104 and a memory 108 communicatively connected to the at least a processor 104, the memory 108 containing instructions 112 configuring the at least a processor 104 to perform one or more processes described herein. Computing device 116 may include processor 104 and/or memory 108. Computing device 116 may be configured to perform one or more processes described herein.

Still referring to FIG. 1, computing device 116 may include but is not limited to, for example, a computing device or cluster of computing devices in a first location and a second computing device or cluster of computing devices in a second location. Computing device 116 may include one or more computing devices dedicated to data storage, security, distribution of traffic for load balancing, and the like. Computing device 116 may distribute one or more computing tasks as described below across a plurality of computing devices of computing device, which may operate in parallel, in series, redundantly, or in any other manner used for distribution of tasks or memory between computing devices. Computing device 116 may be implemented, as a non-limiting example, using a "shared nothing" architecture.

Still referring to FIG. 1, computing device 116 may be designed and/or configured to perform any method, method step, or sequence of method steps in any embodiment described in this disclosure, in any order and with any degree of repetition. For instance, computing device 116 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 116 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, as used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, in some embodiments, system 100 includes a camera 120. System 100 may, using camera 120, capture image 124 of signal 128. Image 124 may include a digital image. As used herein, a "camera" is a set of one or more devices configured to detect electromagnetic radiation. Camera 120 may detect, in non-limiting examples, visible light, infrared light, and ultraviolet light. Camera 120 may generate a representation of detected electromagnetic radiation, such as an image. In some cases, a camera may include one or more optics. Non-limiting examples of optics include spherical lenses, aspherical lenses, reflectors, polarizers, filters, windows, aperture stops, and the like. In some cases, camera 120 may include an image sensor. Exemplary non-limiting image sensors include digital image sensors, such as without limitation charge-coupled device (CCD) sensors and complimentary metal-oxide-semiconductor (CMOS) sensors, chemical image sensors, and analog image sensors, such as without limitation film. In some cases, a camera may be sensitive within a non-visible range of electromagnetic radiation, such as without limitation infrared. As used in this disclosure, "image data" is information representing at least a physical scene, space, and/or object. In some cases, image data may be generated by camera 120. "Image data" may be used interchangeably through this disclosure with "image," where image is used as a noun. An image may be optical, such as without limitation where at least an optic is used to generate an image of an object. An image may be material, such as without limitation when film is used to capture an image. An image may be digital, such as without limitation when represented as a bitmap. Alternatively, an image may be comprised of any media capable of representing a physical scene, space, and/or object. Alternatively, where "image" is used as a verb, in this disclosure, it refers to generation and/or formation of an image. In some embodiments, camera 120 may be configured to capture video.

Still referring to FIG. 1, as used herein, a "signal" is a physical record of medical data of a subject. In some embodiments, signal 128 may include a paper readout of medical data produced by a device which records such data from a sensor. Signal 128 may include, in non-limiting examples, electrocardiogram (ECG) data, electroencephalogram (EEG) data, X-ray data, MRI data, CT scan data, and pathology test data. In a non-limiting example, signal 128 may include a physical printout of such data. In some embodiments, signal 128 may include a measurement of activity of a subject's heart. In some embodiments, signal 128 may include ECG data. In some embodiments, signal 128 may include time series data. In some embodiments, signal 128 may include a plurality of parallel recordings of time-series data, such as in a 12 lead ECG.

Still referring to FIG. 1, in some embodiments, system 100 includes network interface device 132. As used herein, a "network interface device" is a component which connects a computing device to a computer network. In some embodiments, a network interface device may include a network interface card. A network interface device may, for example, interpret data received over a computer network and/or transmit data over a computer network. Such computer networks may include, in non-limiting examples, wired or wireless computer networks. In some embodiments, system 100 is communicatively connected to repository 140 of deidentified patient health information 136. Such communicative connection may be implemented using network interface device 132. As used herein, "deidentified patient health information" is medical data of one or more subjects which does not include identifying information of the one or more subjects. In some embodiments, deidentified patient health information 136 includes aggregated data. In some embodiments, deidentified patient health information 136 includes data on individual subjects. Deidentified patient health information 136 may include, in non-limiting examples, ECG data of a subject, and one or more medical conditions of the subject.

Still referring to FIG. 1, deidentified patient health information 136 may be stored in repository 140. Repository 140 may be implemented, without limitation, as a relational database, a key-value retrieval database such as a NOSQL database, or any other format or structure for use as a database that a person skilled in the art would recognize as suitable upon review of the entirety of this disclosure. Repository 140 may alternatively or additionally be implemented using a distributed data storage protocol and/or data structure, such as a distributed hash table or the like. Repository 140 may include a plurality of data entries and/or records as described above. Data entries in repository 140 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure. In some embodiments, system 100 may retrieve deidentified patient health information 136 from repository 140. In some embodiments, system 100 may transmit to repository 140 a query. In some embodiments, system 100 may receive deidentified patient health information 136 from repository 140.

Still referring to FIG. 1, in some embodiments, system 100 includes user interface 144. User interface 144 may include an input interface and/or an output interface. An input interface may include one or more mechanisms by which a user may input data into a computing device, such as, in non-limiting examples, a keyboard, button, mouse, touchscreen, camera, microphone, scroll wheel, trackpad, switch, lever, or controller. An output interface may include one or more mechanisms by which a computing device may display information to a user, such as, in non-limiting examples, a screen, speaker, or haptic feedback system. As used herein, a device "displays" a datum if the device outputs the datum in a format suitable for communication to a user. For example, a device may display a datum by outputting text or an image on a screen or outputting a sound using a speaker.

Still referring to FIG. 1, in some embodiments, system 100 may crop image 124. System 100 may crop image 124 such that a region of image 124 not depicting signal 128 is removed. As used herein, an image is "cropped" when its dimensions are reduced such that a segment of a previous version of an image is no longer within the boundaries of the image. In some embodiments, system 100 may remove information from image 124 without reducing dimensions of image 124. For example, system 100 may remove a segment of image 124 within the boundaries of image 124 such as by changing that section to transparent or a solid color. In some embodiments, image 124 is cropped such that a remaining portion of image 124 includes signal 128 and/or includes only signal 128. In some embodiments, system 100 may crop image 124 as a function of a region of interest. In a non-limiting example, system 100 may crop image 124 such that a region of interest is preserved. In another non-limiting example, system 100 may crop image 124 such that a region of interest and other regions identified using connected component analysis are preserved. In another non-limiting example, system 100 may segment image 124 and crop image 124 such that one or more segments are preserved, such as segments including a region of interest. In some embodiments, a region of interest may be determined using an edge detection technique. In a non-limiting example, one or more edges of a physical document including signal 128, such as an edge of a piece of paper including signal 128, may be detected, and a region of interest may include a region between such edges. In some embodiments, a region of interest may be determined using an object detection technique. In a non-limiting example, a machine learning model may be trained on a dataset including example images associated with example locations of signals within such images, and such machine learning model may be used to identify a region of an image which contains a signal. Determination of regions of interest, connected component analysis, and segmentation of images are described below.

Still referring to FIG. 1, in some embodiments, system 100 may determine calibration datum 152. System 100 may determine calibration datum 152 using one or more image processing steps and/or a machine vision system. In some embodiments, one or more image processing steps are applied to enhance clarity of image 124, as described below. In some embodiments, a machine vision system is used to recognize signal 128 within image 124. In some embodiments, signal 128 may be oriented (such as rotated) into a consistent position, such as upright.

Still referring to FIG. 1, in some embodiments, system 100 may determine calibration datum 152 using user interface 144. As used herein, a "calibration datum" is a category of a signal, a parameter of a signal, an orientation of a signal, a scale of a signal, or a combination thereof. Such a category of a signal may include, in a non-limiting example, an ECG (as opposed to another type of signal). Such a parameter of a signal may include, in a non-limiting example, a number of leads used to generate ECG data. Such an orientation of a signal may include, in a non-limiting example, an ECG being horizontal and reading left to right. Such a scale of a signal may include, in a non-limiting example, a number of mm/s of a physical record of an ECG. In a non-limiting example, system 100 may present to user 148, by user interface 144, image 124 and prompt user 148 to properly orient image 124, and calibration datum 152 may be determined as a function of user 148 orientation of image 124. In another non-limiting example, system 100 may present to user 148, by user interface 144, image 124 and prompt user 148 to verify orientation of image 124, and calibration datum 152 may be determined as a function of user verification and/or any adjustments to image 124 made by user 148 in response to such prompt. In some embodiments, calibration datum 152 may be determined without user input. In a non-limiting example, a machine learning model may be trained to recognize properly calibrated images and/or to determine optimal settings for one or more aspects of calibration such as orientation of image 124.

Still referring to FIG. 1, in some embodiments, system 100 may include a machine vision system. In some embodiments, a machine vision system may include at least a camera. A machine vision system may use images, such as images from at least a camera, to make a determination about a scene, space, and/or object. For example, in some cases a machine vision system may be used for world modeling or registration of objects within a space. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and φ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure.

Still referring to FIG. 1, an exemplary machine vision camera is an OpenMV Cam H7 from OpenMV, LLC of Atlanta, Georgia, U.S.A. OpenMV Cam comprises a small, low power, microcontroller which allows execution of machine vision applications. OpenMV Cam comprises an ARM Cortex M7 processor and a 640×480 image sensor operating at a frame rate up to 150 fps. OpenMV Cam may be programmed with Python using a Remote Python/Procedure Call (RPC) library. OpenMV CAM may be used to operate image classification and segmentation models, such as without limitation by way of TensorFlow Lite; detection motion, for example by way of frame differencing algorithms; marker detection, for example blob detection; object detection, for example face detection; eye tracking; person detection, for example by way of a trained machine learning model; camera motion detection, for example by way of optical flow detection; code (barcode) detection and decoding; image capture; and video recording.

Still referring to FIG. 1, system 100 may include an image processing module. As used in this disclosure, an "image processing module" is a component of a device designed to process digital images. In an embodiment, image processing module may include a plurality of software algorithms that can analyze, manipulate, or otherwise enhance image 124 such as, without limitation, a plurality of image processing techniques as described below. In another embodiment, image processing module may slow include hardware components such as, without limitation, one or more graphics processing units (GPUs) that can accelerate the processing of large amount of images. In some cases, image processing module may be implemented with one or more image processing libraries such as, without limitation, OpenCV, PIL/Pillow, ImageMagick, and the like. In some embodiments, a plurality of images may be processed. For example, multiple images may be captured of multiple signals and/or multiple segments of the same signal, and each such image may be processed. In another example, multiple images may be captured of the same signal, image processing may be performed, a best image may be determined, and the best image may be used in further steps.

Still referring to FIG. 1, image processing module may be configured to receive plurality of images from at least a camera 120. In a non-limiting example, image processing module may be configured to receive the plurality of images by generating a first image capture parameter, transmitting a command to at least an camera 120 to take at least a first image of the plurality of images with the first image capture parameter, generating a second image capture parameter, transmitting a command to at least an camera 120 to take at least a second image of the plurality of images with the second image capture parameter, and receiving, from at least an camera 120, at least a first image and at least second image. In another non-limiting example, plurality of images may be taken by at least a camera 120 using the same image capture parameter. Image capture parameter may be generated as a function of user input.

Still referring to FIG. 1, at least an image may be transmitted from at least a camera 120 to image processing module via any suitable electronic communication protocol, including without limitation packet-based protocols such as transfer control protocol-internet protocol (TCP-IP), file transfer protocol (FTP) or the like. In some embodiments, plurality of images may be transmitted via a text messaging service such as simple message service (SMS) or the like. plurality of images may be received via a portable memory device such as a disc or "flash" drive, via local and/or near-field communication (NFC), or according to any other direct or indirect means for transmission and/or transfer of digital images. Receiving plurality of images may include retrieval of plurality of images from a data store containing plurality of images as described below; for instance, and without limitation, plurality of images may be retrieved using a query that, for instance, specifies a timestamp that one or more images may be required to match.

Still referring to FIG. 1, image processing module may be configured to process plurality of images. In an embodiment, image processing module may be configured to compress and/or encode plurality of images to reduce the file size and storage requirements while maintaining the essential visual information (e.g., visual information of signal 128) need for further processing steps as described below. In an embodiment, compression and/or encoding of plurality of images may facilitate faster transmission of plurality of images. In some cases, image processing module may be configured to perform a lossless compression on plurality of images, wherein the lossless compression may maintain the original image quality of plurality of images. In a non-limiting example, image processing module may utilize one or more lossless compression algorithms, such as, without limitation, Huffman coding, Lempel-Ziv-Welch (LZW), Run-Length Encoding (RLE), and/or the like to identify and remove redundancy in each image of plurality of images without losing any information. In such embodiment, compressing and/or encoding each image of plurality of images may include converting the file format of each image into PNG, GIF, lossless JPEG2000 or the like. In an embodiment, plurality of images compressed via lossless compression may be perfectly reconstructed to the original form (e.g., original image resolution, dimension, color representation, format, and the like) of plurality of images. In other cases, image processing module may be configured to perform a lossy compression on plurality of images, wherein the lossy compression may sacrifice some image quality of plurality of images to achieve higher compression ratios. In a non-limiting example, image processing module may utilize one or more lossy compression algorithms, such as, without limitation, Discrete Cosine Transform (DCT) in JPEG or Wavelet Transform in JPEG2000, discard some less significant information within plurality of images, resulting in a smaller file size but a slight loss of image quality of plurality of images. In such embodiment, compressing and/or encoding each image of plurality of images may include converting the file format of each image into JPEG, WebP, lossy JPEG2000, or the like.

Still referring to FIG. 1, in an embodiment, processing plurality of images may include determining a degree of quality of depiction of signal 128 for each image of plurality of images. As used in this disclosure, a "degree of quality of depiction" of signal 128 is the degree to which image clearly depicts a signal 128. In an embodiment, image processing module may determine a degree of blurriness of each image of plurality of images. In a non-limiting example, image processing module may perform a blur detection by taking a Fourier transform, or an approximation such as a Fast Fourier Transform (FFT) of each image of plurality of images and analyzing a distribution of low and high frequencies in the resulting frequency-domain depiction of each image of plurality of images; for instance, and without limitation, numbers of high-frequency values below a threshold level may indicate blurriness. In another non-limiting example, detection of blurriness may be performed by convolving each image of plurality of images, a channel of each image of plurality of images, or the like with a Laplacian kernel; for instance, and without limitation, this may generate a numerical score reflecting a number of rapid changes in intensity shown in each image, such that a high score indicates clarity and a low score indicates blurriness. In some cases, blurriness detection may be performed using a Gradient-based operator, which measures operators based on the gradient or first derivative of each image of plurality of images, based on the hypothesis that rapid changes indicate sharp edges in the image, and thus are indicative of a lower degree of blurriness. In some cases, blur detection may be performed using Wavelet-based operator, which takes advantage of the capability of coefficients of the discrete wavelet transform to describe the frequency and spatial content of plurality of images. In some cases, blur detection may be performed using statistics-based operators take advantage of several image statistics as texture descriptors in order to compute a focus level. In other cases, blur detection may be performed by using discrete cosine transform (DCT) coefficients in order to compute a focus level of each image of plurality of images from its frequency content. Additionally, or alternatively, image processing module may be configured to rank plurality of images according to degree of quality of depiction of signal 128 and select a highest-ranking image from plurality of images.

Still referring to FIG. 1, processing plurality of images may include enhancing at least an image containing signal 128 via a plurality of image processing techniques to improve the quality (or degree of quality of depiction) of at least an image for better processing and analysis as described further in this disclosure. In an embodiment, image processing module may be configured to perform a noise reduction operation on at least an image containing signal 128, wherein the noise reduction operation may remove or minimize noise (arises from various sources, such as sensor limitations, poor lighting conditions, image compression, and/or the like), resulting in a cleaner and more visually coherent image. In some cases, noise reduction operation may be performed using one or more image filters; for instance, and without limitation, noise reduction operation may include Gaussian filtering, median filtering, bilateral filtering, and/or the like. Noise reduction operation may be done, by image processing module, by averaging or filtering out pixel values in neighborhood of each pixel of at least an image to reduce random variations.

Still referring to FIG. 1, in another embodiment, image processing module may be configured to perform a contrast enhancement operation on at least an image containing signal 128. In some cases, at least an image may exhibit low contrast, making signal 128 difficult to distinguish from the background. Contrast enhancement operation may improve the contrast of at least an image containing signal 128 by stretching the intensity range of at least an image and/or redistributing the intensity values (i.e., degree of brightness or darkness of a pixel in at least an image). In a non-limiting example, intensity value may represent the gray level or color of each pixel, scale from 0 to 255 in intensity range for an 8-bit image, and scale from 0 to 16,777,215 in a 24-bit color image. In some cases, contrast enhancement operation may include, without limitation, histogram equalization, adaptive histogram equalization (CLAHE), contrast stretching, and/or the like. image processing module may be configured to adjust the brightness and darkness levels within the at least an image to make signal 128 more distinguishable (i.e., increase degree of quality of depiction). Additionally, or alternatively, image processing module may be configured to perform a brightness normalization operation to correct variations in lighting conditions (i.e., uneven brightness levels). In some cases, at least an image may include a consistent brightness level across the entire signal 128 after brightness normalization operation performed by image processing module. In a non-limiting example, image processing module may perform a global or local mean normalization, where the average intensity value of the entire image or signal 128 may be calculated and used to adjust the brightness levels.

Still referring to FIG. 1, in some embodiments, image processing module may be configured to perform a color space conversion operation to increase degree of quality of depiction. In a non-limiting example, in case of color image (i.e., RGB image), image processing module may be configured to convert RGB image to grayscale or HSV color space. Such conversion may emphasize the differences in intensity values between signal 128 and the background. image processing module may further be configured to perform an image sharpening operation such as, without limitation, unsharp masking, Laplacian sharpening, high-pass filtering, and/or the like. image processing module may use image sharpening operation to enhance the edges and fine details related to signal 128 within at least an image by emphasizing high-frequency components within at least an image.

Still referring to FIG. 1, processing plurality of images may include isolating signal 128 from at least an image as a function of plurality of image processing techniques. At least an image may include highest-ranking image selected by image processing module as described above. In an embodiment, plurality of image processing techniques may include one or more morphological operations, wherein the morphological operations are techniques developed based on set theory, lattice theory, topology, and random functions used for processing geometrical structures using a structuring element. A "structuring element," for the purpose of this disclosure, is a small matrix or kernel that defines a shape and size of a morphological operation. In some cases, structing element may be centered at each pixel of at least an image and used to determine an output pixel value for that location. In a non-limiting example, isolating signal 128 from at least an image may include applying a dilation operation, wherein the dilation operation is a basic morphological operation configured to expand or grow the boundaries of objects in at least an image. In another non-limiting example, isolating signal 128 from at least an image may include applying an erosion operation, wherein the erosion operation is a basic morphological operation configured to shrink or erode the boundaries of objects in at least an image. In another non-limiting example, isolating signal 128 from at least an image may include applying an opening operation, wherein the opening operation is a basic morphological operation configured to remove small objects or thin structures from at least an image while preserving larger structures. In a further non-limiting example, isolating signal 128 from at least an image may include applying a closing operation, wherein the closing operation is a basic morphological operation configured to fill in small gaps or holes in objects in at least an image while preserving the overall shape and size of the objects. These morphological operations may be performed by image processing module to enhance the edges of objects, remove noise, or fill gaps in signal 128 before further processing.

Still referring to FIG. 1, in an embodiment, isolating signal 128 from at least an image may include utilizing an edge detection technique, which may detect one or more shapes defined by edges. An "edge detection technique," as used in this disclosure, includes a mathematical method that identifies points in a digital image, such as, without limitation, at least an image, at which the image brightness changes sharply and/or has discontinuities. In an embodiment, such points may be organized into straight and/or curved line segments, which may be referred to as "edges." Edge detection technique may be performed, by image processing module, using any suitable edge detection algorithm, including without limitation Canny edge detection, Sobel operator edge detection, Prewitt operator edge detection, Laplacian operator edge detection, and/or Differential edge detection. Edge detection technique may include phase congruency-based edge detection, which finds all locations of an image where all sinusoids in the frequency domain, for instance as generated using a Fourier decomposition, may have matching phases which may indicate a location of an edge. Edge detection technique may be used to detect a shape of, in a non-limiting example, an edge of paper on which signal 128 is printed; in an embodiment, edge detection technique may be used to find closed figures formed by edges.

Still referring to FIG. 1, in some embodiments, isolating signal 128 from at least an image may include determining a region of interest (ROI) via edge detection technique. As used in this disclosure, a "region of interest" is a specific area within a digital image that contains information relevant to a signal. In a non-limiting example, image information located outside ROI may include irrelevant or extraneous information such as, without limitation, objects in background of an image. Such portion of image containing irrelevant or extraneous information may be disregarded, by image processing module. In some cases, ROI may vary in size, shape, and/or location within at least an image. In a non-limiting example ROI may be presented as a rectangular bounding box (length×width) around signal 128 on at least an image. In some cases, ROI may specify one or more coordinates of one or more corners of rectangular bounding box, and/or length and/or width of rectangular bounding box around signal 128 on at least an image. image processing module may then be configured to isolate signal 128 from the at least an image based on ROI. In a non-limiting example, and without limitation, image processing module may crop at least an image according to rectangular bounding box around signal 128.

Still referring to FIG. 1, image processing module may be configured to perform a connected component analysis (CCA) on at least an image for signal 128 isolation. As used in this disclosure, a "connected component analysis (CCA)," also known as connected component labeling, is an image processing technique used to identify and label connected regions within a binary image (i.e., an image which each pixel having only two possible values: 0 or 1, black or white, or foreground and background). "Connected regions," as described herein, is a group of adjacent pixels that share the same value and are connected based on a predefined neighborhood system such as, without limitation, 4-connected or 8-connected neighborhoods. In some cases, image processing module may convert at least an image into a binary image via a thresholding process, wherein the thresholding process may involve setting a threshold value that separates the pixels of at least an image corresponding to the signal 128 (foreground) from those corresponding to the background. Pixels with intensity values above the threshold may be set to 1 (white) and those below the threshold may be set to 0 (black). In an embodiment, CCA may be employed to detect and extract signal 128 by identifying a plurality of connected regions that exhibit specific properties or characteristics of signal 128. image processing module may then filter plurality of connected regions by analyzing plurality of connected regions properties such as, without limitation, area, aspect ratio, height, width, perimeter, and/or the like. In a non-limiting example, connected components that closely resemble the dimensions and aspect ratio of signal 128 may be retained, by image processing module, while other components may be discarded.

Still referring to FIG. 1, in an embodiment, isolating signal 128 from at least an image may include segmenting signal 128 into a plurality of signal 128 sub-regions. Segmenting signal 128 into plurality of signal 128 sub-regions may include segmenting signal 128 as a function of ROI and/or CCA via an image segmentation process. As used in this disclosure, an "image segmentation process" is a process for partition a digital image, such as, without limitation, an image, into one or more segments, wherein each segment represents a distinct part of the image. Image segmentation process may change the representation of plurality of images. Image segmentation process may be performed, by image processing module, via one or more image segmentation techniques. In a non-limiting example, image processing module may perform a region-based segmentation, wherein the region-based segmentation involves growing regions from one or more seed points or pixels on at least an image based on a similarity criterion. Similarity criterion may include, without limitation, color, intensity, texture, and/or the like. In a non-limiting example, region-based segmentation may include region growing, region merging, watershed algorithms, and the like.

Still referring to FIG. 1, in some embodiments, system 100 may generate an augmented image as a function of image 124 using a trained augmented image machine learning model. In some embodiments, system 100 may train an augmented image machine learning model by receiving raw data, generating a direct data digital image from the raw data, printing a physical image as a function of the raw data, generating a first scanned digital image by capturing an image of the physical image using a camera, and, using the direct data digital image and the first scanned digital image to train a machine learning model to generate a transformed digital image from a second scanned digital image. Such raw data may include, for example, voltage time series data received from a set of electrodes which measures electrical activity of the heart. Such direct data digital image may include, for example, a digital image plotting the raw data over time. Such direct data digital image and first scanned digital image may form a pair to be used as part of a training data set. Many such data pairs may be collected based on data, such as ECG data, of a variety of subjects. Such data pairs may make up a training dataset which is used to train augmented image machine learning model. Augmented image machine learning model may be trained such that it accepts as an input a scanned digital image (such as a picture of a paper ECG) and outputs an augmented image. Augmented image 124 may be generated using a device and/or process disclosed in U.S. patent application Ser. No. 18/652,364, filed on May 1, 2024, and titled "APPARATUS AND METHOD FOR TRAINING A MACHINE LEARNING MODEL TO AUGMENT SIGNAL DATA AND IMAGE DATA", the entirety of which is hereby incorporated by reference.

Still referring to FIG. 1, in some embodiments, where signal 128 includes ECG data, system 100 may convert image 124 into time-series data describing the ECG data. Such time-series data may be used to generate a new image of the ECG data. In some embodiments, such a new image and/or an augmented image may be used in place of image 124 in one or more processes described herein. Conversion of image 124 into time-series data and/or generation of an image from such time-series data may be performed using a device and/or process disclosed in U.S. patent application Ser. No. 18/641,217, filed on Apr. 19, 2024, and titled "SYSTEMS AND METHODS FOR TRANSFORMING ELECTROCARDIOGRAM IMAGES FOR USE IN ONE OR MORE MACHINE LEARNING MODELS", and/or U.S. patent application Ser. No. 18/591,499, filed on Feb. 29, 2024, and titled "APPARATUS AND METHOD FOR TIME SERIES DATA FORMAT CONVERSION AND ANALYSIS," the entirety of each of which is hereby incorporated by reference.

Still referring to FIG. 1, in some embodiments, system 100 determines signal metric 156 as a function of image 124. As used herein, a "signal metric" is a measurement of a signal, a measurement of a feature of a signal, or both. In non-limiting examples, where a signal includes ECG data, a signal metric may include a measurement of a PR interval, RR interval, ST interval, TP interval, QT interval, P wave duration, PR segment, QRS duration, ST segment, P axis, and number of beats per minute. In another example, where a signal includes ECG data, a signal metric may include a rhythm type, such as a sinus rhythm. In some embodiments, signal metric 156 is selected from the list consisting of a PR interval, a QRS duration, a P axis, and a number of beats per minute. In a non-limiting example, signal metric 156 may include a measurement of a first feature of a signal relative to a second feature of a signal. Signal metric 156 may be determined using a machine vision system. For example, a machine vision system may be used to determine one or more peaks of ECG data, and a distance between peaks may be used to determine an RR interval. In another example, a machine vision system may be used to determine a slope of one or more points and/or segments of ECG data and/or rate of change of such a slope, and such data may be used to determine a QRS duration. In some embodiments, signal metric 156 may be determined using a signal metric machine learning model. In some embodiments, a signal metric machine learning model may be trained using a supervised learning algorithm. A signal metric machine learning model may be trained on a training dataset including example images, associated with example signal metrics. Such a training dataset may be generated by, for example, collecting images of signals, and associating them with historical signal metrics manually determined by specialists based on those signals. In some embodiments, generation of signal metric 156 may include embedding image 124. Embedding image 124 may include generation of a numerical representation of image 124. In some embodiments, such a numerical representation may include a vector, where similarity between vectors across multiple inputs indicate similarity between inputs. In some embodiments, a machine learning model, such as a convolutional neural network, may be used to create such a numerical representation. Non-limiting examples of convolutional neural networks for embedding image data include VGG (Visual Geometry Group), ResNet (Residual Networks), Inception (GoogLeNet) and EfficientNet. In some embodiments, one or more preprocessing steps may be applied prior to embedding image 124. For example, image 124 may be resized and/or normalized in order to make it suitable for input into a machine learning model trained to generate an embedding. In some embodiments, embedding image data may be used to reduce dimensionality of high dimensional data. In some embodiments, embedding image data may be used to extract features from image data. In some embodiments, an embedding may be input into signal metric machine learning model, and signal metric 156 may be received as an output. In some embodiments, signal metric 156 and/or an embedding used to determine signal metric 156 may be generated using a device and/or process disclosed in U.S. patent application Ser. No. 18/230,043, filed on Aug. 3, 2023, and titled "APPARATUS AND A METHOD FOR GENERATING A DIAGNOSTIC LABEL," the entirety of which is hereby incorporated by reference.

Still referring to FIG. 1, in some embodiments, system 100 may determine signal metric position 160 as a function of signal metric 156. As used herein, a "signal metric position" is a data structure describing the position of a signal metric relative to that of one or more members of a population. As a non-limiting example, a signal metric position may indicate that a subject's PR interval is higher than 55% of a population. In some embodiments, a population restriction may be identified, and a population which a user's signal metric is compared to may be determined according to a population restriction. As used herein, a "population restriction" is a data structure setting a boundary on individuals to be considered members of a population. In non-limiting examples, population restrictions may include a limitation that members of a population be male, and a limitation that members of a population be under 25 years old. In a non-limiting example, determination of signal metric position 160 may include the following steps: determination of signal metric 156 as described herein, retrieval of a plurality of instances of a like metric of members of a population conforming to a population restriction or retrieval of data describing a distribution of such metric among members of a population, and comparison of signal metric 156 to such metrics. In some embodiments, retrieval of a like metric of members of a population and/or retrieval of data describing a distribution of such metric may include generation of a query requesting such information from a database, such as repository 140, transmission of such query to repository 140, and receipt of a response. In a non-limiting example, signal metric 156 may be compared to like metrics of members of a population in order to determine a percentage of like metrics which signal metric 156 is above.

Still referring to FIG. 1, in some embodiments, system 100 may generate abnormality datum 164. In some embodiments, abnormality datum 164 may be generated as a function of image 124. As used herein, an "abnormality datum" is a data structure describing a difference between a signal and a typical signal of a healthy individual. In a non-limiting example, abnormality datum 164 may include an amount a subject's at rest heart rate is above an at rest heart rate of a healthy individual. In some embodiments, abnormality datum 164 may be determined as a function of signal metric 156 and/or signal metric position 160. In some embodiments, system 100 may generate abnormality datum 164 based on signal metric 156 being above or below a threshold. A threshold may be determined as a function of information about a subject associated with signal 128, such as age, sex, medical history, and the like. In another non-limiting example, system 100 may generate abnormality datum 164 based on signal metric position 160 being above or below a threshold. In a non-limiting example, system 100 may generate abnormality datum 164 if signal metric position 160 indicates that signal metric 156 is in the top 5% of a population.

Still referring to FIG. 1, in some embodiments, system 100 may determine medical condition datum 168. As used herein, a "medical condition datum" is a data structure identifying in a subject an ailment, a lack of an ailment, a likelihood of an ailment, or a combination thereof. For example, medical condition datum 168 may indicate that a subject has a particular disease. In another example, medical condition datum 168 may indicate that a subject does not have a particular disease. In another example, medical condition datum 168 may indicate that a subject is healthy. In another example, medical condition datum 168 may indicate that a subject has a first disease and does not have a second disease. In another example, medical condition datum 168 may indicate that a subject has a high likelihood of having a particular disease. Diseases which medical condition datum 168 may identify include, in non-limiting examples, an infectious disease, a deficiency disease, a hereditary disease, and a physiological disease. In some embodiments, system 100 may display medical condition datum 168 to user 148. Display of information to a user is described below.

Still referring to FIG. 1, in some embodiments, system 100 may determine medical condition datum 168 by identifying a similarity between signal metric 156 and deidentified patient health information 136 of repository 140 and generating medical condition datum 168 as a function of the similarity. As used herein, a "similarity" between a first datum and a second datum is a data structure describing the numerical distance between the first datum and the second datum, a data structure describing whether the first datum and the second datum are members of the same category, or both. As a non-limiting example, a similarity may include a comparison between a first subject's heart rate while resting with heart rates while resting of a population. In some embodiments, a similarity may be determined between abnormality datum 164 and deidentified patient health information 136 of repository 140, and medical condition datum 168 may be generated as a function of such similarity. In some embodiments, a similarity may be determined which accounts for multiple signal metrics and/or other information relating to a subject such as age, sex, ethnicity, levels of physical activity, diet, medications the subject is on, and other aspects of subject's medical history. In a non-limiting example, system 100 may determine signal metric 156 from signal 128, query repository 140 for deidentified patient health information with metrics within a range of signal metric 156, receive deidentified patient health information 136 from repository 140, and determine medical condition datum 168 as a function of medical conditions of received deidentified patient health information 136. Generation of abnormality datum 164 and/or similarity may be performed using a device and/or process disclosed in U.S. patent application Ser. No. 18/652,921, filed on May 2, 2024, and titled "AN APPARATUS AND METHOD FOR CLASSIFYING A USER TO A COHORT OF RETROSPECTIVE USERS", the entirety of which is hereby incorporated by reference.

Still referring to FIG. 1, in some embodiments, system 100 may generate medical condition datum 168 using a medical condition machine learning model. Medical condition machine learning model may be trained using a supervised learning algorithm. Medical condition machine learning model may be trained on a training dataset including example images, signal metrics, abnormality data, and/or calibration data, associated with example medical conditions. Such a training dataset may be obtained by, for example, gathering diagnoses of historical subjects and associating those diagnoses with images of ECG data of those subjects. Once medical condition machine learning model is trained, it may be used to determine medical condition datum 168. System 100 may input image 124, signal metric 156, calibration datum 152, and/or abnormality datum 164 into medical condition machine learning model, and system 100 may receive medical condition datum 168 from the model.

Still referring to FIG. 1, in some embodiments, system 100 may generate medical condition confidence score 172. In some embodiments, medical condition machine learning model may output medical condition confidence score 172 in addition to its other outputs. As used herein, a "confidence score" is a degree of confidence that an associated datum is accurate. As used herein, a "medical condition confidence score" is a degree of confidence that a medical condition datum is accurate. In some embodiments, a confidence score may be determined as a function of a machine learning model, such as medical condition machine learning model. Confidence scores may be used to predict how likely a model output is to be accurate. For example, in some classifiers, numerical values are calculated, and a cutoff value is used to determine which category the input fits into. In this example, the numerical value may be used to determine a certainty score based on how closely it fits into a class and/or how close to a decision boundary it is. In another example, in clustering algorithms, certainty scores may be calculated based on how closely an input fits into a cluster. In some embodiments, medical condition datum 168 may be generated without the use of medical condition machine learning model, and medical condition confidence score 172 may be generated using other methods. For example, where medical condition datum 168 is determined as a function of a comparison between signal metric 156 and a threshold, medical condition confidence score 172 may be determined as a function of the distance between signal metric 156 and the threshold. In a non-limiting example, signal 128 may include ECG data, signal metric 156 may include a prediction of a subject's left ventricular ejection fraction (LVEF) based on such ECG data, and abnormality datum 164 may be determined based on a comparison between the LVEF prediction and a threshold. For example, abnormality datum 164 may be determined if such LVEF prediction is below a threshold.

Still referring to FIG. 1, in some embodiments, system 100 may select medical condition machine learning model from a plurality of medical condition machine learning models. In some embodiments, such selection may be performed as a function of calibration datum 152. In a non-limiting example, different medical condition machine learning models may be applied to images of different signal types, and calibration datum 152 may indicate a type of signal 128 that image 124 depicts (such as ECG data), such as based on user input.

Still referring to FIG. 1, in some embodiments, system 100 may identify guidance on treatment of a medical condition as a function of medical condition datum 168. For example, system 100 may retrieve from a database guidance on best practices for treatment and/or prevention of a medical condition associated with medical condition datum 168. In some embodiments, retrieved guidance may include guidance published by a relevant medical association. In some embodiments, system 100 may identify guidance using a web search, such as a keyword search. In some embodiments, system 100 may identify guidance using a machine learning model, such as a language model trained on medical publications. Guidance on treatment of a medical condition may be displayed to user 148. In some embodiments, identification of a medical condition, verification of a medical condition, and/or identification of guidance on a medical condition may be performed as described in U.S. patent application Ser. No. 18/648,059, filed on Apr. 26, 2024, and titled "APPARATUS AND METHODS FOR GENERATING DIAGNOSTIC HYPOTHESES BASED ON BIOMEDICAL SIGNAL DATA", the entirety of which is hereby incorporated by reference.

Still referring to FIG. 1, in some embodiments, system 100 may generate quality diagnostic 176 of image 124. In some embodiments, quality diagnostic 176 is generated by extracting a plurality of signal metrics from signal 128; validating signal 128 by classifying signal 128 to a plurality of preliminary signal metrics; and determining an accuracy status of the extracted plurality of signal metrics by comparing the plurality of preliminary signal metrics to the extracted plurality of signal metrics; and generating the quality diagnostic based on validation of signal 128. In some embodiments, quality diagnostic 176 may identify an error in a medical procedure used to record signal 128, and/or an error in another step such as capturing of image 124 of signal 128, and/or processing of image 124. In some embodiments, system 100 may alert user 148 as to an error identified by quality diagnostic 176. This may allow user 148 to, for example, record a new, more accurate, set of data. For example, system 100 may capture a second image of signal 128 as a function of quality diagnostic 176. Generation and use of quality diagnostic 176 may be performed using a device and/or process disclosed in U.S. patent application Ser. No. 18/599,435, filed on Mar. 8, 2024, and titled "AN APPARATUS AND METHOD FOR GENERATING A QUALITY DIAGNOSTIC OF ECG (ELECTROCARDIOGRAM) DATA," the entirety of which is hereby incorporated by reference.

Still referring to FIG. 1, in some embodiments, system 100 may display one or more elements of data described herein to user 148. In some embodiments, display of information to user 148 may be performed using user interface 144. In non-limiting examples, signal metric 156, signal metric position 160, abnormality datum 164, abnormality datum confidence score 172, guidance on treatment of a medical condition, image 124, and/or calibration datum 152 may be displayed to user 148 through user interface 144.

Still referring to FIG. 1, in some embodiments, system 100 may generate a map indicating at least a region of signal 128 which indicates an abnormality and display the map overlayed on image 124. Such a map may be generated by, for example, inputting a plurality of subsets of image 124 into abnormality datum machine learning model and determining from outputs of the model which segments of image 124 lead most to generation of abnormality datum 164. In some embodiments system 100 may generate a map indicating the regions of image 124 associated with signal metric 156 used to generate abnormality datum 164. In a non-limiting example, if abnormality datum 164 is determined as a function of P wave of an ECG, then system 100 may generate and display a map highlighting a P wave and may display to user 148 the map overlayed on image 124. Generation of a map, capture of image 124, and/or display of data to user 148 may be performed using a device and/or process disclosed in U.S. patent application Ser. No. 18/653,235, filed on May 2, 2024, and titled "APPARATUS AND METHODS FOR IDENTIFYING ABNORMAL BIOMEDICAL FEATURES WITHIN IMAGES OF BIOMEDICAL DATA", the entirety of which is hereby incorporated by reference.

Still referring to FIG. 1, in some embodiments, a datum may be displayed to a user using a visual element and/or a visual element data structure. A visual element data structure may include a visual element. As used herein, a "visual element" is a datum that is displayed visually to a user. In some embodiments, a visual element data structure may include a rule for displaying visual element. In some embodiments, a visual element data structure may be determined as a function of datum such as a map. In some embodiments, a visual element data structure may be determined as a function of an item from the list consisting of signal metric 156, signal metric position 160, abnormality datum 164, abnormality datum confidence score 172, guidance on treatment of a medical condition, image 124, and calibration datum 152. In a non-limiting example, a visual element data structure may be generated such that visual element describing or highlighting a segment of image 124 is displayed to a user 148. Additional examples are provided below with reference to FIGS. 5-12. In some embodiments, visual element may include one or more elements of text, images, shapes, charts, particle effects, interactable features, and the like. In some embodiments, a visual element data structure may include rules governing if or when visual element is displayed. In a non-limiting example, a visual element data structure may include a rule causing a visual element describing datum to be displayed when a user selects the datum using a graphical user interface (GUI).

Still referring to FIG. 1, a visual element data structure may include rules for presenting more than one visual element, or more than one visual element at a time. In an embodiment, about 1, 2, 3, 4, 5, 10, 20, or 50 visual elements may be displayed simultaneously.

Still referring to FIG. 1, a visual element data structure rule may apply to a single visual element or datum, or to more than one visual element or datum. For example, a visual element data structure may rank visual elements and/or other data and/or apply numerical values to them, and a computing device may display a visual element as a function of such rankings and/or numerical values. A visual element data structure may apply rules based on a comparison between such a ranking or numerical value and a threshold. In a non-limiting example, multiple instances of abnormality data may be generated, and visual elements associated with individual instances of abnormality data may be ranked based on associated abnormality datum confidence scores.

Still referring to FIG. 1, in some embodiments, visual element may be interacted with. For example, visual element may include an interface, such as a button or menu. In some embodiments, visual element may be interacted with using a user device such as a smartphone.

Still referring to FIG. 1, in some embodiments, system 100 may transmit visual element to a display. A display may communicate visual element to user 148. A display may include, for example, a smartphone screen, a computer screen, or a tablet screen. A display may be configured to provide a visual interface. A visual interface may include one or more virtual interactive elements such as, without limitation, buttons, menus, and the like. A display may include one or more physical interactive elements, such as buttons, a computer mouse, or a touchscreen, which allow user 148 to input data into the display. Interactive elements may be configured to enable interaction between a user and a computing device. In some embodiments, a visual element data structure is determined as a function of data input by user 148 into a display.

Still referring to FIG. 1, a variable and/or datum described herein may be represented as a data structure. In some embodiments, a data structure may include one or more functions and/or variables, as a class might in object-oriented programming. In some embodiments, a data structure may include data in the form of a Boolean, integer, float, string, date, and the like. In a non-limiting example, a rhythm data structure may include a string value representing a text description of the rhythm type. In some embodiments, data in a data structure may be organized in a linked list, tree, array, matrix, tenser, and the like. In some embodiments, a data structure may include or be associated with one or more elements of metadata. A data structure may include one or more self-referencing data elements, which processor 104 may use in interpreting the data structure. In a non-limiting example, a data structure may include "<date>" and "</date>," tags, indicating that the content between the tags is a date.

Still referring to FIG. 1, in some embodiments, a data structure may be read and/or manipulated by processor 104. In a non-limiting example, an image data structure may be read and input into a machine learning model.

Still referring to FIG. 1, in some embodiments, a data structure may be calibrated. In some embodiments, a data structure may be trained using a machine learning algorithm. In a non-limiting example, a data structure may include an array of data representing the biases of connections of a neural network. In this example, the neural network may be trained on a set of training data, and a back propagation algorithm may be used to modify the data in the array. Machine learning models and neural networks are described further herein.

Figure 2:
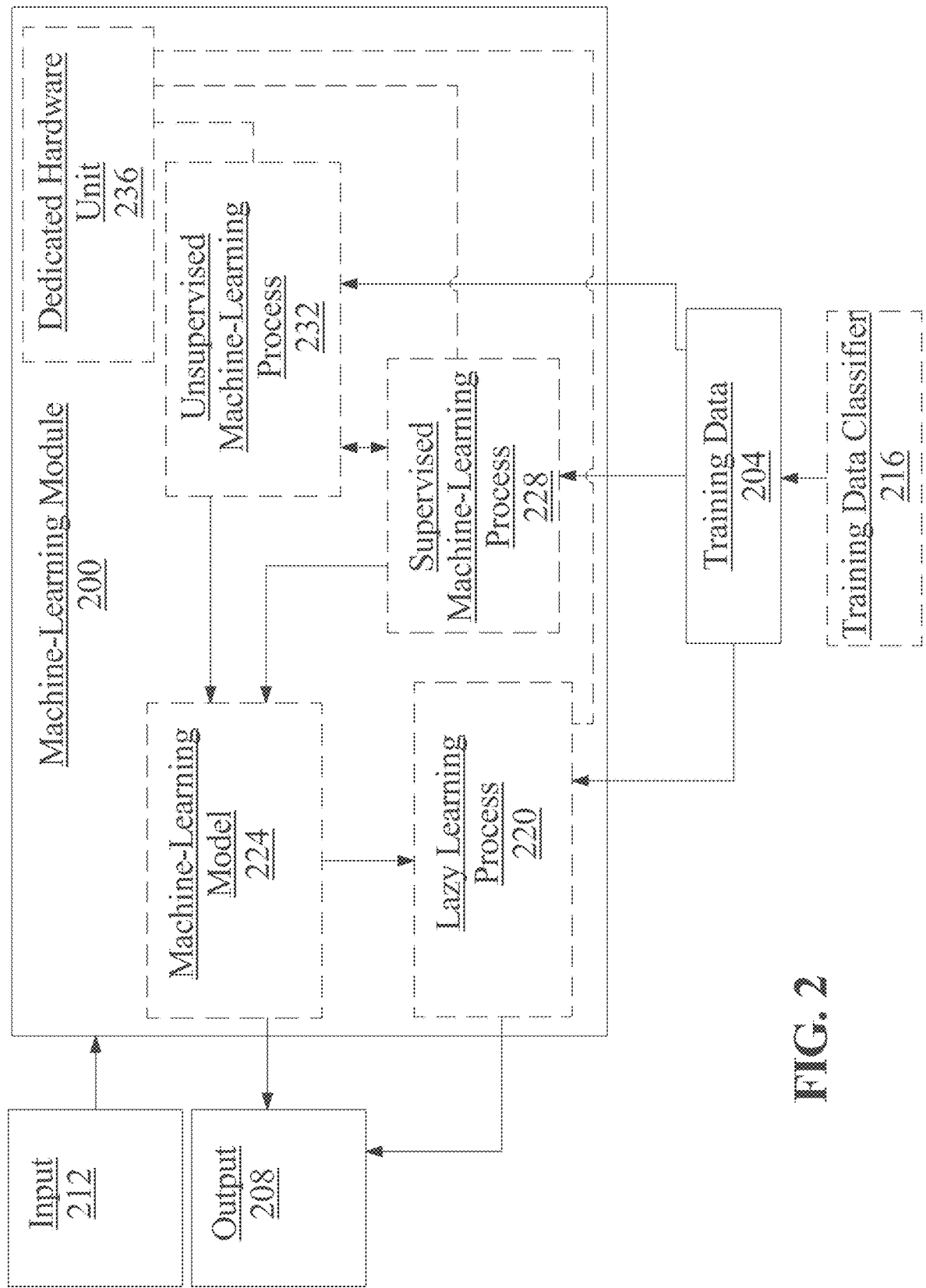
FIG. 2 is a box diagram of an exemplary machine learning model.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, an input may include image 124 and an output may include abnormality datum 164.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to particular types of signal or particular types of medical condition.

Still referring to FIG. 2, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 2, training examples for use as training data may be selected from a population of potential examples according to cohorts relevant to an analytical problem to be solved, a classification task, or the like. Alternatively, or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 2, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively, or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 2, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 2, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}:X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the 25$^{th}$ percentile value and the 50$^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 2, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively, or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include image data as described above as inputs, abnormality data as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

With continued reference to FIG. 2, system 100 may use user feedback to train the machine-learning models and/or classifiers described above. For example, classifier may be trained using past inputs and outputs of classifier. In some embodiments, if user feedback indicates that an output of classifier was "bad," then that output and the corresponding input may be removed from training data used to train classifier, and/or may be replaced with a value entered by, e.g., another user that represents an ideal output given the input the classifier originally received, permitting use in retraining, and adding to training data; in either case, classifier may be retrained with modified training data as described in further detail below. In some embodiments, training data of classifier may include user feedback.

With continued reference to FIG. 2, in some embodiments, an accuracy score may be calculated for classifier using user feedback. For the purposes of this disclosure, "accuracy score," is a numerical value concerning the accuracy of a machine-learning model. For example, a plurality of user feedback scores may be averaged to determine an accuracy score. In some embodiments, a cohort accuracy score may be determined for particular cohorts of persons. For example, user feedback for users belonging to a particular cohort of persons may be averaged together to determine the cohort accuracy score for that particular cohort of persons and used as described above. Accuracy score or another score as described above may indicate a degree of retraining needed for a machine-learning model such as a classifier; system 100 may perform a larger number of retraining cycles for a higher number (or lower number, depending on a numerical interpretation used), and/or may collect more training data for such retraining, perform more training cycles, apply a more stringent convergence test such as a test requiring a lower mean squared error, and/or indicate to a user and/or operator that additional training data is needed.

Figure 3:
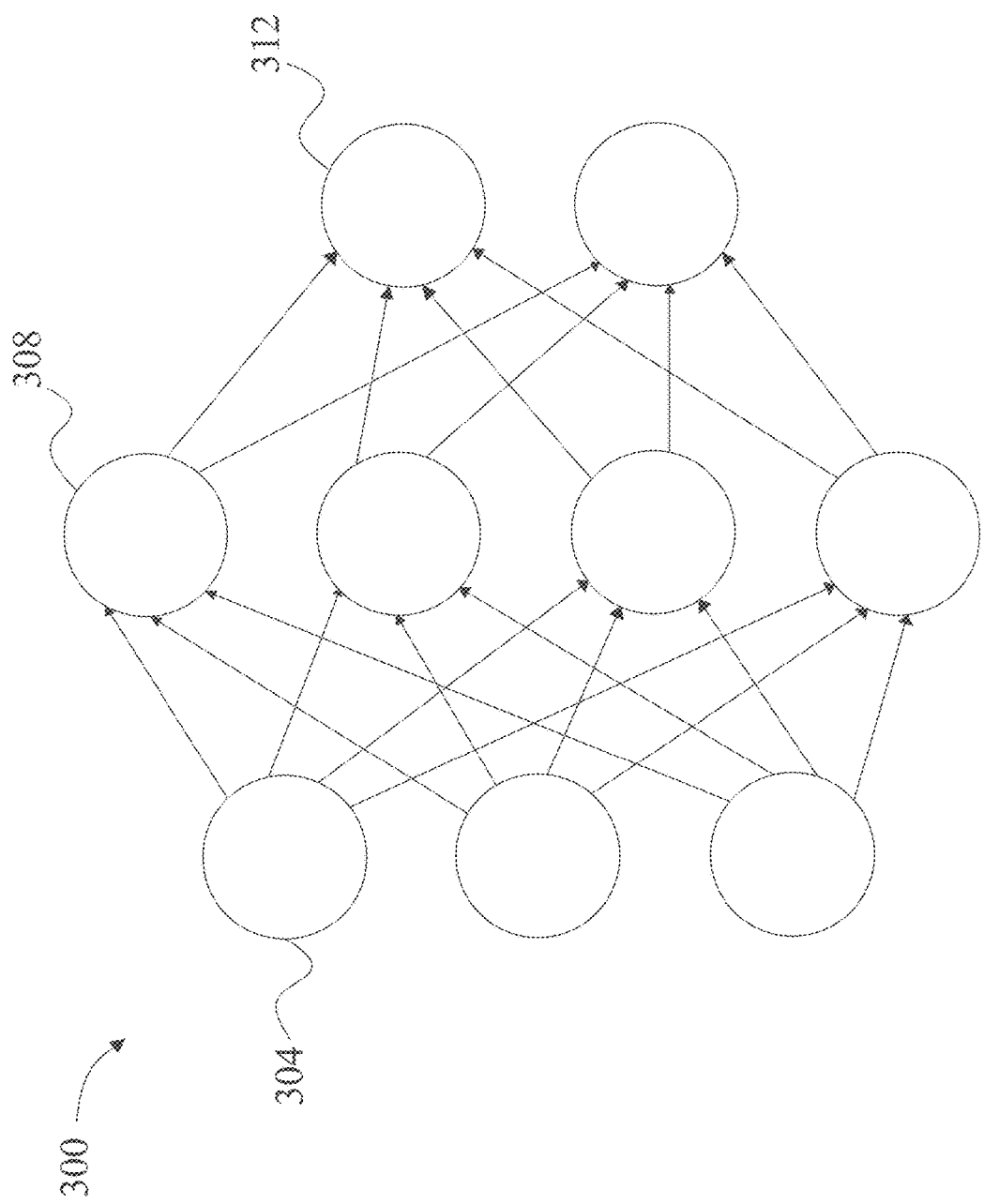
FIG. 3 is a diagram of an exemplary neural network.

Referring now to FIG. 3, an exemplary embodiment of neural network 300 is illustrated. A neural network 300, also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
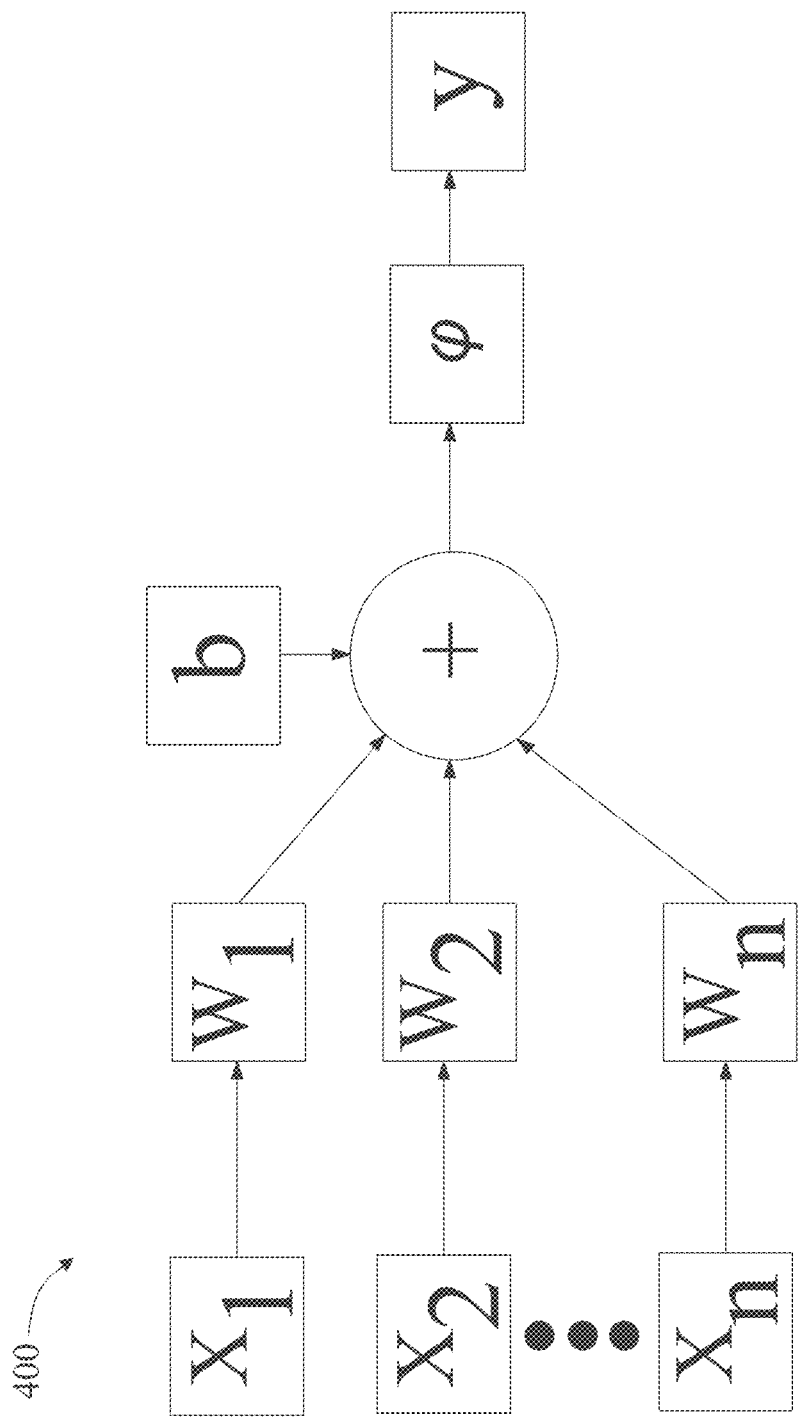
FIG. 4 is a diagram of an exemplary neural network node.

Referring now to FIG. 4, an exemplary embodiment of a node 400 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x) = \tanh^2(x)$, a rectified linear unit function such as $f(x) = \max(0, x)$, a "leaky" and/or "parametric" rectified linear unit function such as $f(x) = \max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x) = x * \text{sigmoid}(x)$, a Gaussian error linear unit function such as $f(x) = a(1 + \tanh(\sqrt{2/\pi}(x + bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Still referring to FIG. 4, a "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like. CNN may include, without limitation, a deep neural network (DNN) extension, where a DNN is defined as a neural network with two or more hidden layers.

Still referring to FIG. 4, in some embodiments, a convolutional neural network may learn from images. In nonlimiting examples, a convolutional neural network may perform tasks such as classifying images, detecting objects depicted in an image, segmenting an image, and/or processing an image. In some embodiments, a convolutional neural network may operate such that each node in an input layer is only connected to a region of nodes in a hidden layer. In some embodiments, the regions in aggregate may create a feature map from an input layer to the hidden layer. In some embodiments, a convolutional neural network may include a layer in which the weights and biases for all nodes are the same. In some embodiments, this may allow a convolutional neural network to detect a feature, such as an edge, across different locations in an image.

Figure 5:
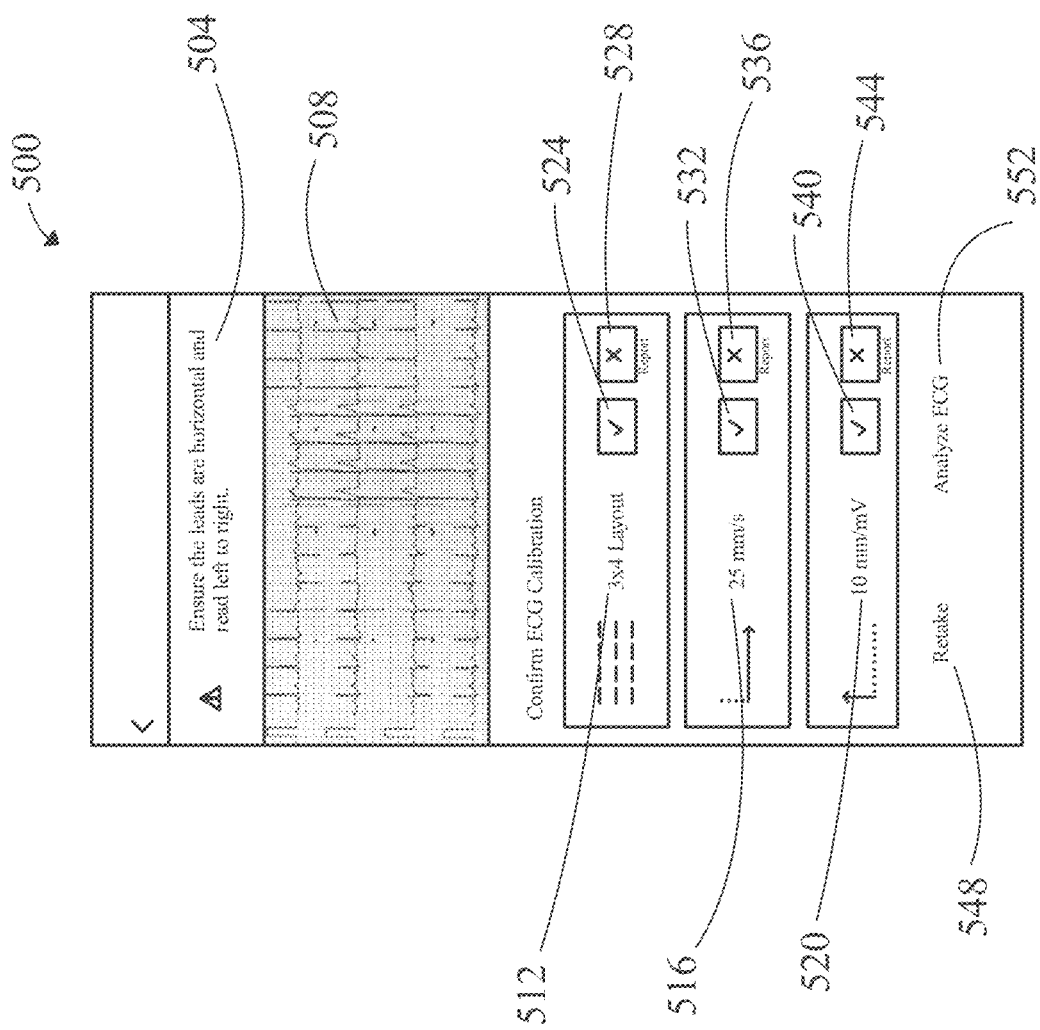
FIG. 5 is an illustration of an exemplary user interface.

Referring now to FIG. 5, an exemplary embodiment of a user interface 500 is provided. User interface 500 may include prompt 504. Prompt 504 may include, for example, instructions for a user. For example, instructions may describe to user how to properly input calibration datum. User interface 500 may include image 508. Image 508 may include an image of a signal as described above. Image 508 may include a raw image and/or an image which has undergone one or more processing steps as described above. User interface 500 may include one or more elements of calibration data such as elements 512, 516 and 520. User interface 500 may include one or more interactive elements used to determine a calibration datum such as elements 524, 528, 532, 536, 540, and 544. User interface 500 may include an interactive element which may be used to cause system 100 to capture a new image, such as element 548. User interface 500 may include an interactive element which may be used to initiate one or more steps described herein, such as element 552.

Figure 6:
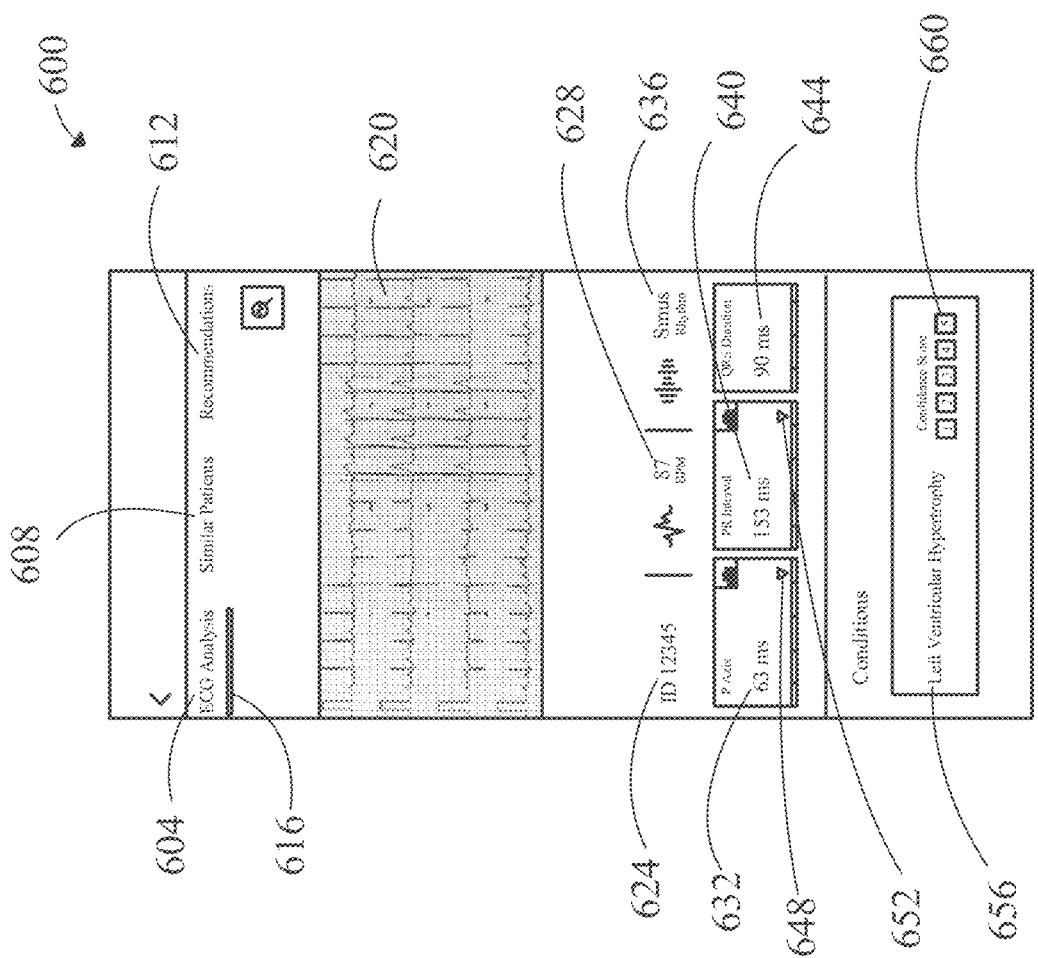
FIG. 6 is an illustration of an exemplary user interface.

Referring now to FIG. 6, an exemplary embodiment of a user interface 600 is provided. User interface 600 may include one or more interactive elements by which a user may select varying functions of system 100, such as elements 604, 608, and 612. User interface 600 may include an element which indicates a function currently selected, such as element 616. User interface 600 may include image 620. Image 620 may include an image of a signal as described above. Image 620 may include a raw image and/or an image which has undergone one or more processing steps as described above. User interface 600 may include an identification number 624 for a particular signal and/or image. User interface 600 may include one or more signal metrics, such as signal metrics 628, 632, 636, 640, and 644. User interface 600 may include one or more signal metric positions, such as signal metric positions 648 and 652. User interface 600 may include a medical condition datum such as medical condition datum 656 and/or one or more medical condition confidence scores such as medical condition confidence score 660 associated with such medical condition data.

Figure 7:
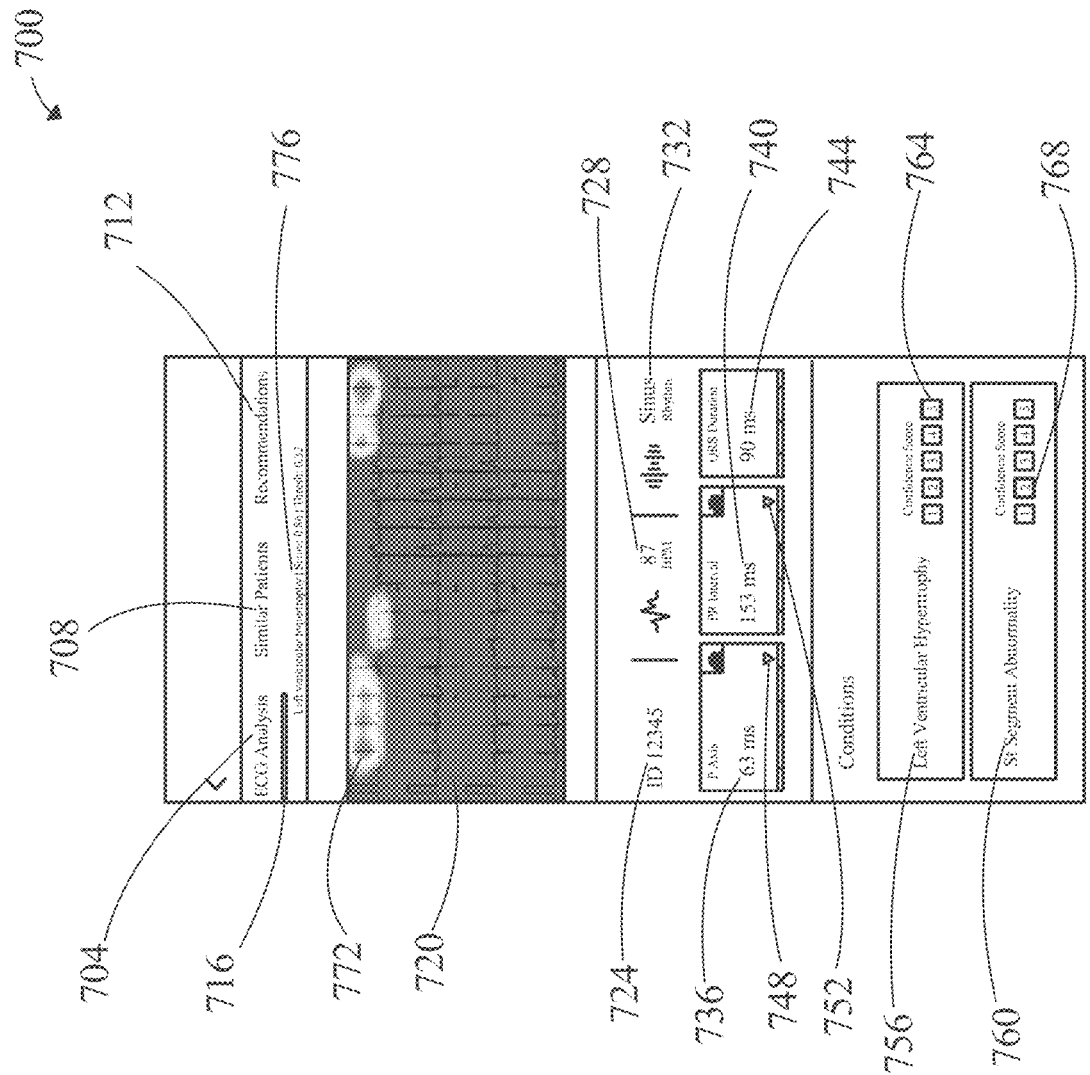
FIG. 7 is an illustration of an exemplary user interface.

Referring now to FIG. 7, an exemplary embodiment of a user interface 700 is provided. User interface 700 may include one or more interactive elements by which a user may select varying functions of system 100, such as elements 704, 708, and 712. User interface 700 may include an element which indicates a function currently selected, such as element 716. User interface 700 may include image 720. Image 720 may include an image of a signal as described above. Image 720 may include a raw image and/or an image which has undergone one or more processing steps as described above. User interface 700 may include an identification number 724 for a particular signal and/or image. User interface 700 may include one or more signal metrics, such as signal metrics 728, 732, 736, 740, and 744. User interface 700 may include one or more signal metric positions, such as signal metric positions 748 and 752. User interface 700 may include one or more elements of medical condition data such as medical condition data 756 and 760 and/or one or more medical condition confidence scores such as medical condition confidence scores 764 and 768 associated with such medical condition data. User interface 700 may include map 772 indicating regions which contribute to determination of a medical condition datum. User interface 700 may include an indicator 776 indicating which medical condition map 772 is referring to, an associated medical condition confidence score, and/or an associated threshold, such as a threshold for a signal metric or a threshold for a confidence score.

Figure 8:
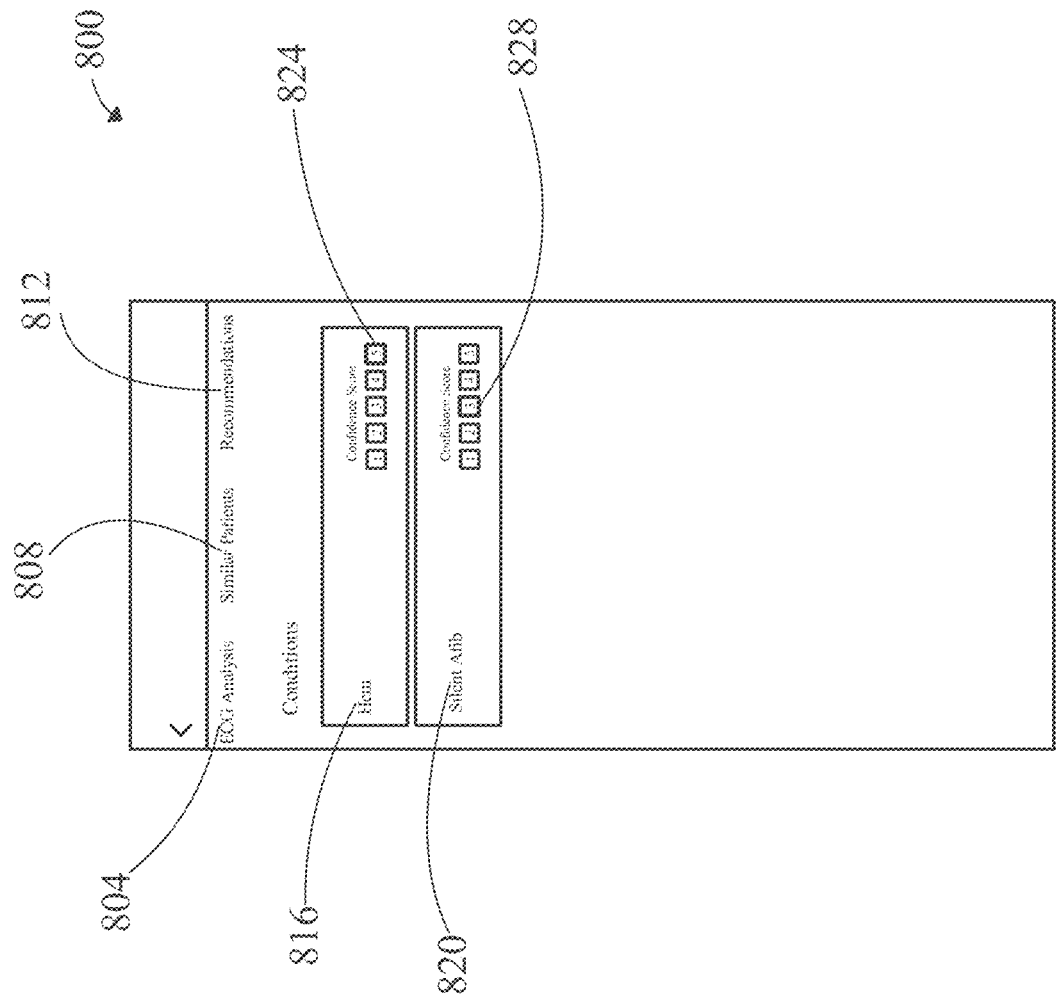
FIG. 8 is an illustration of an exemplary user interface.

Referring now to FIG. 8, an exemplary embodiment of a user interface 800 is provided. User interface 800 may include one or more interactive elements by which a user may select varying functions of system 100, such as elements 804, 808, and 812. User interface 800 may include one or more elements of medical condition data such as medical condition data 816 and 820 and/or one or more medical condition confidence scores such as medical condition confidence scores 824 and 828 associated with such medical condition data.

Figure 9:
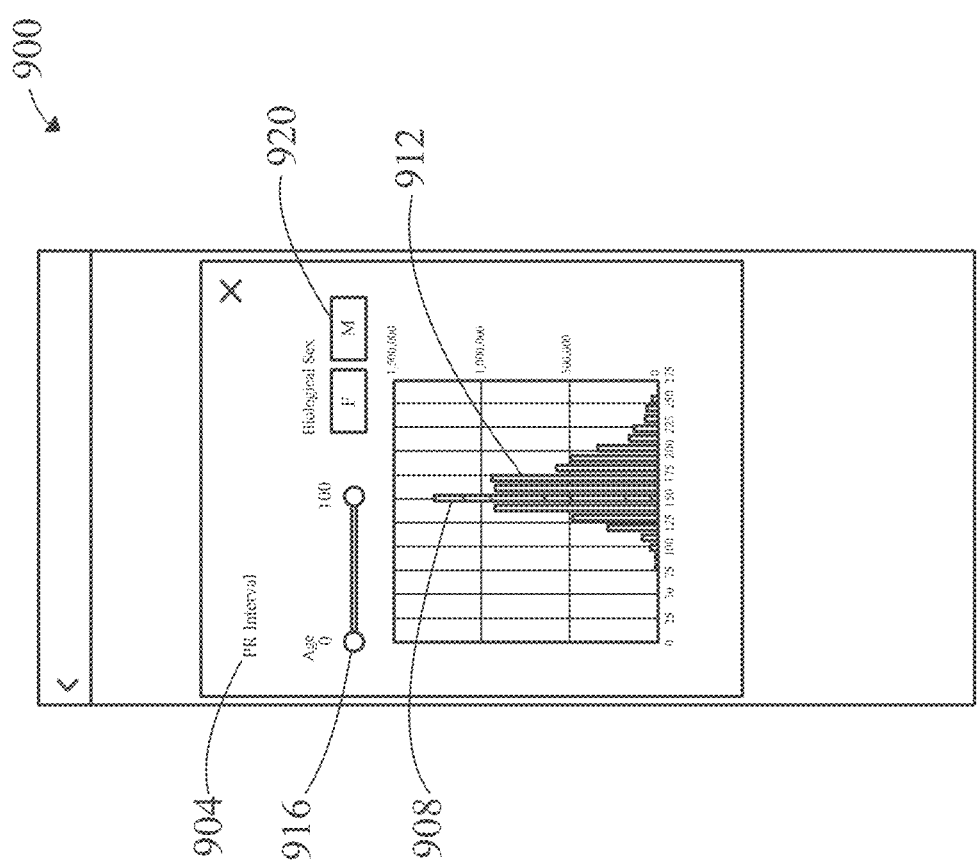
FIG. 9 is an illustration of an exemplary user interface.

Referring now to FIG. 9, an exemplary embodiment of a user interface 900 is provided. User interface 900 may include an identifier 904 of a signal metric such as a name. User interface 900 may include signal metric position 908. User interface 900 may include data 912 of other members of a population as described with reference to FIG. 1. User interface 900 may include one or more sets of interactable features such as 916 and 920. Such sets of interactable features may be used to determine population restrictions as described with reference to FIG. 1. For example, set of interactable features 916 may restrict a population by age and set of interactable features 916 may restrict a population by biological sex.

Figure 10:
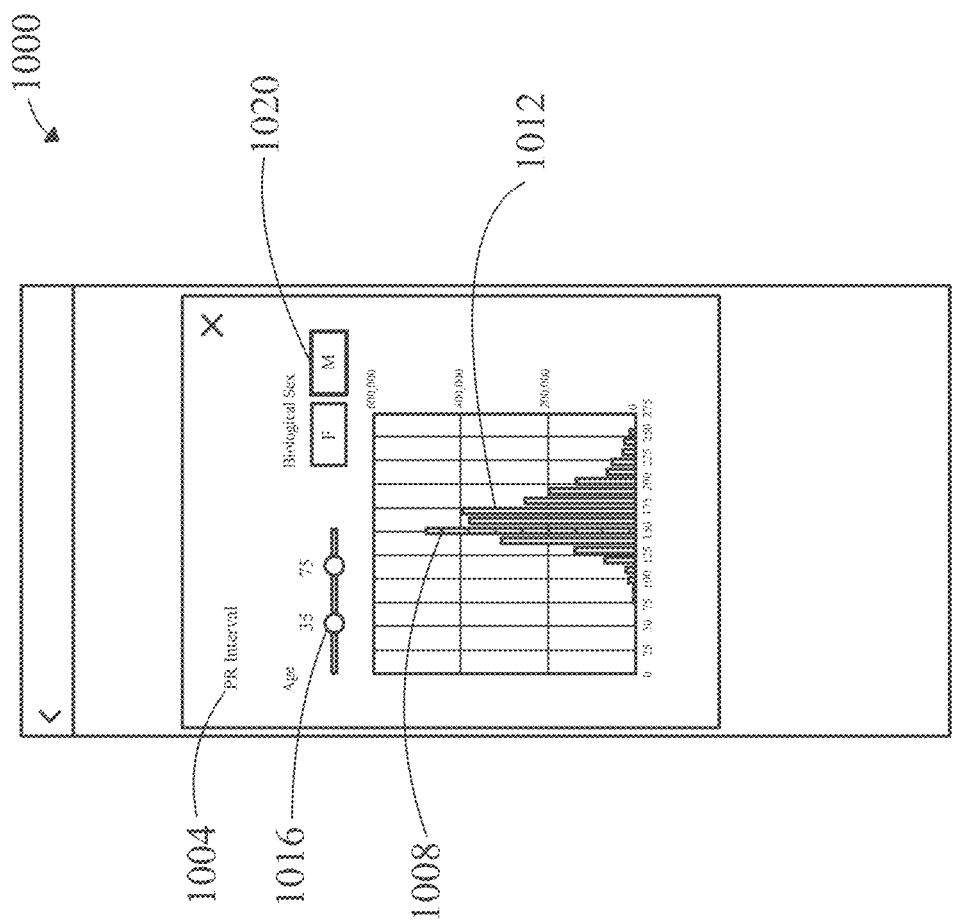
FIG. 10 is an illustration of an exemplary user interface.

Referring now to FIG. 10, an exemplary embodiment of a user interface 1000 is provided. User interface 1000 may include an identifier 1004 of a signal metric such as a name. User interface 1000 may include signal metric position 1008. User interface 1000 may include data 1012 of other members of a population as described with reference to FIG. 1. User interface 1000 may include one or more sets of interactable features such as 1016 and 1020. Such sets of interactable features may be used to determine population restrictions as described with reference to FIG. 1. For example, set of interactable features 1016 may restrict a population by age and set of interactable features 1016 may restrict a population by biological sex.

Figure 11:
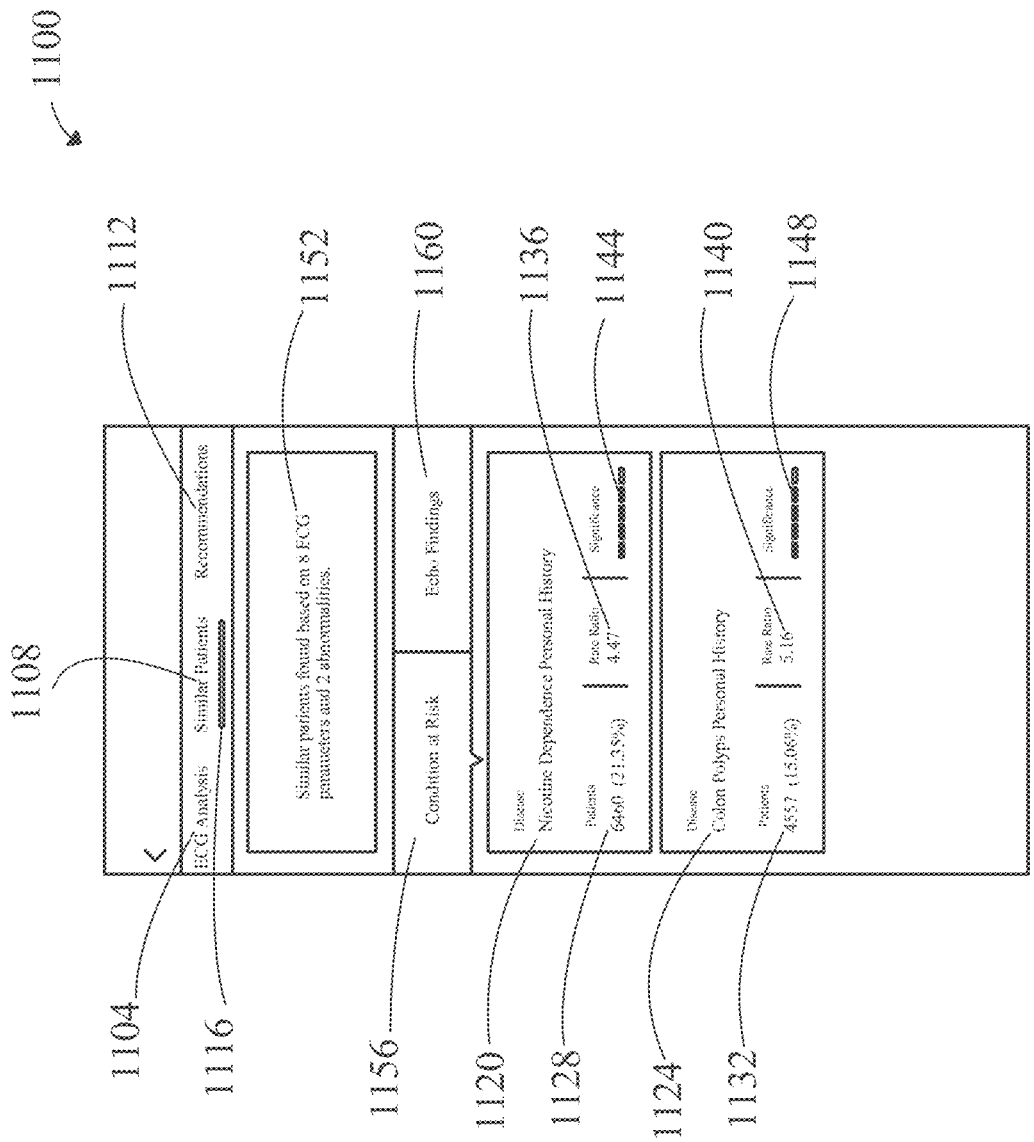
FIG. 11 is an illustration of an exemplary user interface.

Referring now to FIG. 11, an exemplary embodiment of a user interface 1100 is provided. User interface 1100 may include one or more interactive elements by which a user may select varying functions of system 100, such as elements 1104, 1108, and 1112. User interface 1100 may include an element which indicates a function currently selected, such as element 1116. User interface 1100 may include one or more elements of medical condition data 1120 and 1124. User interface 1100 may include descriptions of metrics associated generation of medical condition data 1120 and 1124 based on similarity of one or more signal metrics with medical data of other patients. For example, user interface may include descriptions of metrics 1128 and 1132 (describing numbers and percentages of similar patients), 1136 and 1140 (describing rate ratios), 1144 and 1148 (describing degrees of significance of medical condition data). User interface 1100 may include a description 1152 which may, for example, provide a broad overview of contents of a page of user interface 1100. User interface 1100 may further include one or more interactive elements by which a user may select to access different categories of findings produced by system 100. In a non-limiting example, user interface 1100 may include interactive element 1156, which may be interacted with to display medical conditions identified by system 100. In another non-limiting example, user interface 1100 may include interactive element 1160, which may be interacted with to display one or more determinations based on an echocardiogram. Such determinations may include, for example, an medical condition datum and/or an medical condition confidence score.

Figure 12:
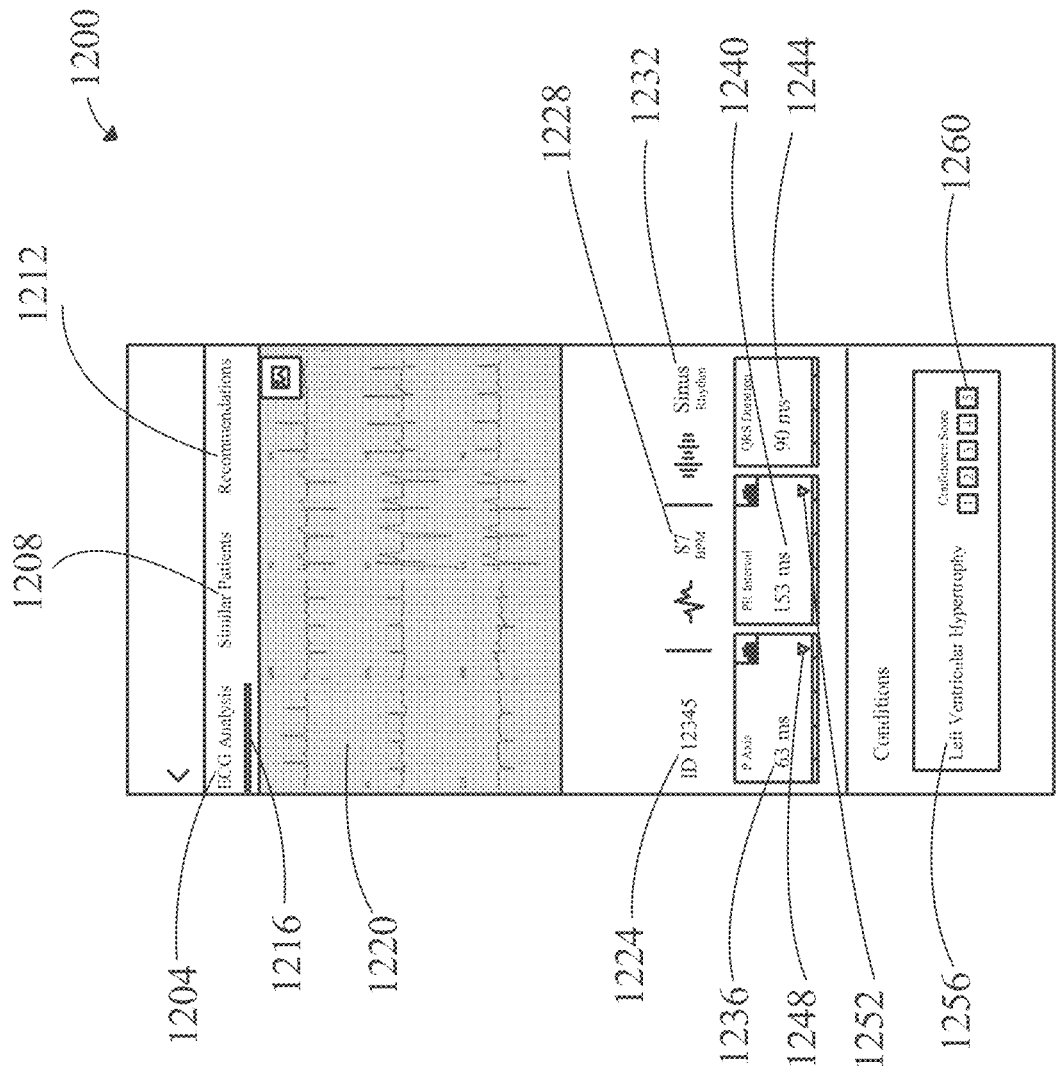
FIG. 12 is an illustration of an exemplary user interface.

Referring now to FIG. 12, an exemplary embodiment of a user interface 1200 is provided. User interface 1200 may include one or more interactive elements by which a user may select varying functions of system 100, such as elements 1204, 1208, and 1212. User interface 1200 may include an element which indicates a function currently selected, such as element 1216. User interface 1200 may include augmented image 1220. Augmented image 1220 may be derived from a previous version of an image as described with respect to FIG. 1. Image 1220 may include a raw image and/or an image which has undergone one or more processing steps as described above. User interface 1200 may include an identification number 1224 for a particular signal and/or image. User interface 1200 may include one or more signal metrics, such as signal metrics 1228, 1232, 1236, 1240, and 1244. User interface 1200 may include one or more signal metric positions, such as signal metric positions 1248 and 1252. User interface 1200 may include one or more elements of medical condition data such as medical condition datum 1256 and/or one or more medical condition confidence scores such as medical condition confidence score 1260 associated with such medical condition data.

Figure 13:
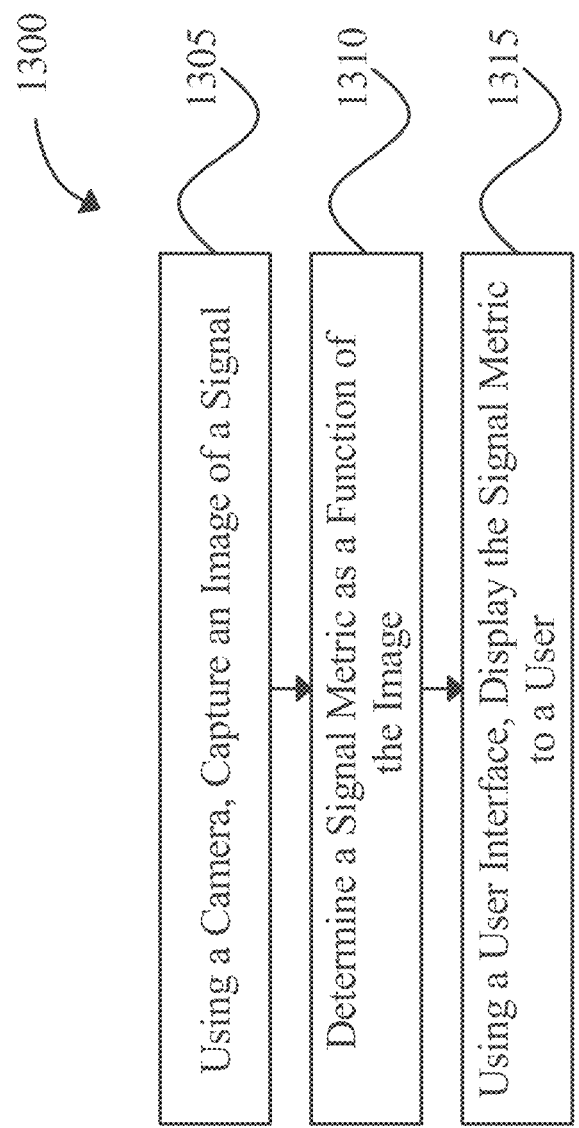
FIG. 13 is a flow diagram depicting an exemplary embodiment of a method of signal digitization.

Referring now to FIG. 13, an exemplary embodiment of a method 1300 of signal digitization is illustrated. One or more steps if method 1300 may be implemented, without limitation, as described with reference to other figures. One or more steps of method 1300 may be implemented, without limitation, using at least a processor. One or more steps if method 1300 may be implemented, without limitation, using a camera, a network interface device, a user interface, and/or a computing device. In some embodiments, a computing device which executes method 1300 may be communicatively connected to a repository of deidentified patient health information.

Still referring to FIG. 13, in some embodiments, method 1300 may include using a camera, capturing an image of a signal 1305.

Still referring to FIG. 13, in some embodiments, method 1300 may include determining a signal metric as a function of the image 1310. In some embodiments, determining the signal metric includes generating an embedding of the image of the signal; and using a signal metric machine learning model, determining the signal metric as a function of the embedding.

Still referring to FIG. 13, in some embodiments, method 1300 may further include generating a medical condition datum as a function of the image; and using the user interface, displaying the medical condition datum to the user. In some embodiments, generating the medical condition datum includes receiving deidentified patient health information from the repository; identifying a similarity between the signal metric and the deidentified patient health information of the repository; and generating the medical condition datum as a function of the similarity. In some embodiments, the medical condition datum may be generated using a trained medical condition machine learning model. In some embodiments, generating the medical condition datum may include selecting the medical condition datum machine learning model from a plurality of medical condition machine learning models as a function of a calibration datum. In some embodiments, method 1300 may further include identifying a medical condition datum confidence score; and using the user interface, display the medical condition confidence score to the user. In some embodiments, method 1300 may further include identifying guidance on treatment of a medical condition as a function of the medical condition datum; and using the user interface, display the guidance to the user.

Still referring to FIG. 13, in some embodiments, method 1300 may include using a user interface, displaying a signal metric to a user 1315. In some embodiments, displaying the medical condition datum to the user includes generating a map indicating at least a region of the signal indicating an abnormality; and using the user interface, displaying to the user the map overlayed on the image.

Still referring to FIG. 13, in some embodiments, method 1300 may further include cropping the image such that a region of the image not depicting the signal is removed. In some embodiments, method 1300 may further include generating a quality diagnostic of the image by extracting a plurality of signal metrics from the signal; validating the signal by classifying the signal to a plurality of preliminary signal metrics; and determining an accuracy status of the extracted plurality of signal metrics by comparing the plurality of preliminary signal metrics to the extracted plurality of signal metrics; and generating the quality diagnostic based on validation of the signal. In some embodiments, method 1300 may further include capturing a second image of the signal as a function of the quality diagnostic. In some embodiments, method 1300 may further include generating, using the user interface, a calibration datum.

Still referring to FIG. 13, in some embodiments, in some embodiments, the signal may include electrocardiogram data. In some embodiments, method 1300 may further include converting the image into time-series data describing the electrocardiogram data. In some embodiments, the signal metric is selected from the list consisting of a PR interval, a QRS duration, a P axis, and a number of beats per minute.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 14:
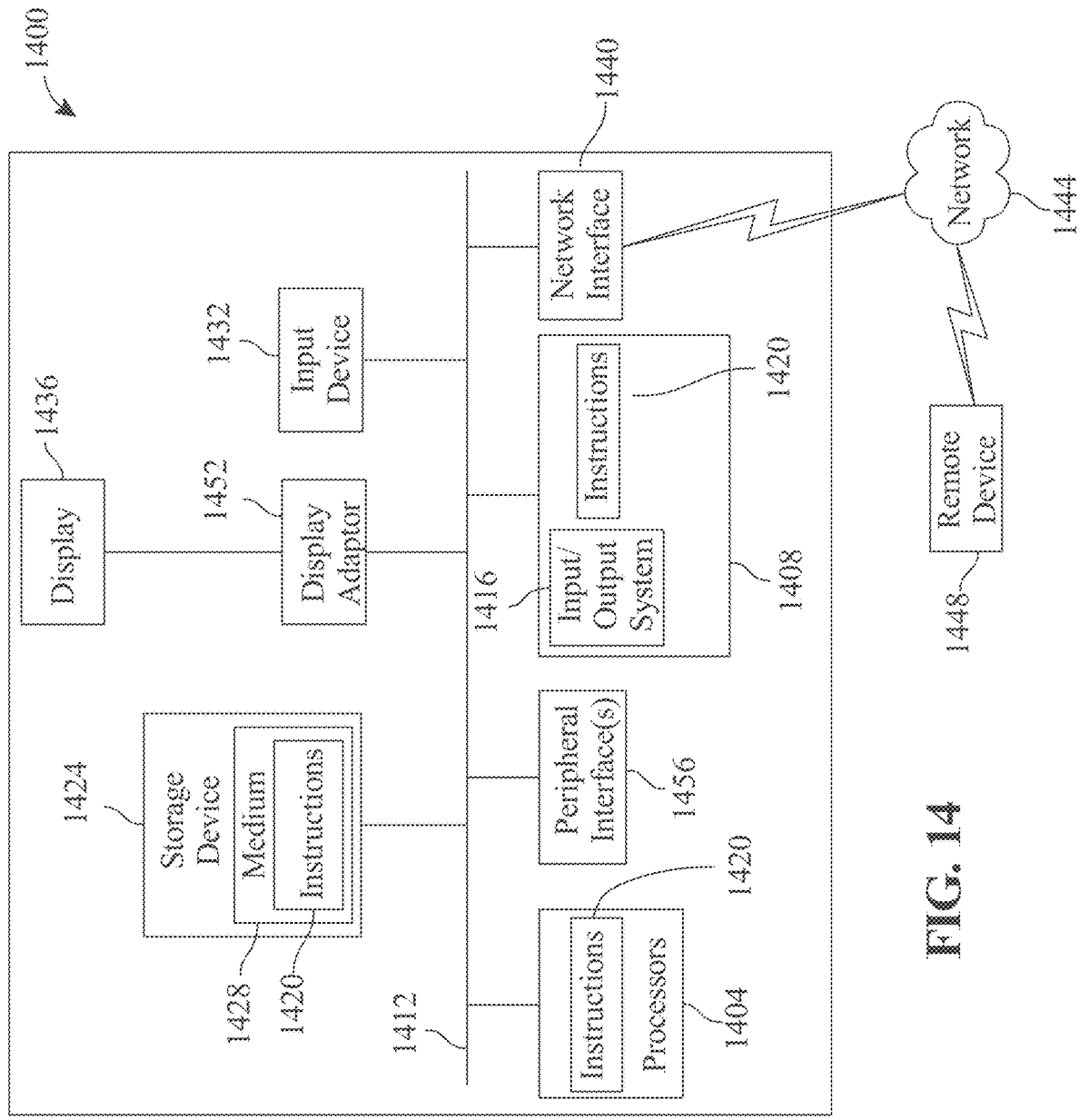
FIG. 14 is a block diagram of a computing system that can be used to implement any one or more of the methodologies disclosed herein and any one or more portions thereof.

FIG. 14 shows a diagrammatic representation of one embodiment of a computing device in the exemplary form of a computer system 1400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1400 includes a processor 1404 and a memory 1408 that communicate with each other, and with other components, via a bus 1412. Bus 1412 may include any of several types of bus structures including, but not limited to, a memory bus, a memory controller, a peripheral bus, a local bus, and any combinations thereof, using any of a variety of bus architectures.

Processor 1404 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1404 may be organized according to Von Neumann and/or Harvard architecture as a non-limiting example. Processor 1404 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1408 may include various components (e.g., machine-readable media) including, but not limited to, a random-access memory component, a read only component, and any combinations thereof. In one example, a basic input/output system 1416 (BIOS), including basic routines that help to transfer information between elements within computer system 1400, such as during start-up, may be stored in memory 1408. Memory 1408 may also include (e.g., stored on one or more machine-readable media) instructions (e.g., software) 1420 embodying any one or more of the aspects and/or methodologies of the present disclosure. In another example, memory 1408 may further include any number of program modules including, but not limited to, an operating system, one or more application programs, other program modules, program data, and any combinations thereof.

Computer system 1400 may also include a storage device 1424. Examples of a storage device (e.g., storage device 1424) include, but are not limited to, a hard disk drive, a magnetic disk drive, an optical disc drive in combination with an optical medium, a solid-state memory device, and any combinations thereof. Storage device 1424 may be connected to bus 1412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1424 (or one or more components thereof) may be removably interfaced with computer system 1400 (e.g., via an external port connector (not shown)). Particularly, storage device 1424 and an associated machine-readable medium 1428 may provide nonvolatile and/or volatile storage of machine-readable instructions, data structures, program modules, and/or other data for computer system 1400. In one example, software 1420 may reside, completely or partially, within machine-readable medium 1428. In another example, software 1420 may reside, completely or partially, within processor 1404.

Computer system 1400 may also include an input device 1432. In one example, a user of computer system 1400 may enter commands and/or other information into computer system 1400 via input device 1432. Examples of an input device 1432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1432 may be interfaced to bus 1412 via any of a variety of interfaces (not shown) including, but not limited to, a serial interface, a parallel interface, a game port, a USB interface, a FIREWIRE interface, a direct interface to bus 1412, and any combinations thereof. Input device 1432 may include a touch screen interface that may be a part of or separate from display device 1436, discussed further below. Input device 1432 may be utilized as a user selection device for selecting one or more graphical representations in a graphical interface as described above.

A user may also input commands and/or other information to computer system 1400 via storage device 1424 (e.g., a removable disk drive, a flash drive, etc.) and/or network interface device 1440. A network interface device, such as network interface device 1440, may be utilized for connecting computer system 1400 to one or more of a variety of networks, such as network 1444, and one or more remote devices 1448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1444, may employ a wired and/or a wireless mode of communication. In general, any network topology may be used. Information (e.g., data, software 1420, etc.) may be communicated to and/or from computer system 1400 via network interface device 1440.

Computer system 1400 may further include a video display adapter 1452 for communicating a displayable image to a display device, such as display device 1436. Examples of a display device include, but are not limited to, a liquid crystal display (LCD), a cathode ray tube (CRT), a plasma display, a light emitting diode (LED) display, and any combinations thereof. Display adapter 1452 and display device 1436 may be utilized in combination with processor 1404 to provide graphical representations of aspects of the present disclosure. In addition to a display device, computer system 1400 may include one or more other peripheral output devices including, but not limited to, an audio speaker, a printer, and any combinations thereof. Such peripheral output devices may be connected to bus 1412 via a peripheral interface 1456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for signal digitization, the system comprising:
   a camera;
   a network interface device;
   a user interface; and
   a computing device configured to:
      using the camera, capture an image of a signal;
      determine a signal metric as a function of the image of the signal;
      generate a medical condition datum as a function of the image using a trained medical condition machine learning model, wherein generating the medical condition datum comprises selecting a medical condition machine learning model from a plurality of medical condition machine learning models as a function of a calibration datum;
      using the user interface, display the signal metric to a user; and
      using the user interface, display the medical condition datum to the user, wherein displaying the medical condition datum comprises:
         generating a map indicating at least a region of the signal indicating an abnormality; and
         using the user interface, displaying to the user the map overlayed on the image;
   wherein the system is communicatively connected to a repository of deidentified patient health information.

2. The system of claim 1, wherein generating the medical condition datum further comprises:
   receiving deidentified patient health information from the repository;
   identifying a similarity between the signal metric and the deidentified patient health information of the repository; and
   generating the medical condition datum as a function of the similarity.

3. The system of claim 1, wherein the computing device is configured to:
   identify a medical condition datum confidence score; and
   using the user interface, display the medical condition confidence score to the user.

4. The system of claim 1, wherein the computing device is configured to:
   identify guidance on treatment of a medical condition as a function of the medical condition datum; and
   using the user interface, display the guidance to the user.

5. The system of claim 1, wherein determining the signal metric comprises:
   generating an embedding of the image of the signal; and
   using a signal metric machine learning model, determining the signal metric as a function of the embedding.

6. The system of claim 1, wherein the computing device is configured to crop the image such that a region of the image not depicting the signal is removed.

7. The system of claim 1, wherein the computing device is configured to generate a quality diagnostic of the image by:
   extracting a plurality of signal metrics from the signal;
   validating the signal by:
      classifying the signal to a plurality of preliminary signal metrics; and
      determining an accuracy status of the extracted plurality of signal metrics by comparing the plurality of preliminary signal metrics to the extracted plurality of signal metrics; and
   generating the quality diagnostic based on validation of the signal.

8. The system of claim 7, wherein the computing device is configured to capture a second image of the signal as a function of the quality diagnostic.

9. The system of claim 1, wherein the computing device is configured to generate, using the user interface, a calibration datum.

10. The system of claim 1, wherein the signal comprises electrocardiogram data.

11. The system of claim 10, wherein the computing device is configured to convert the image into time-series data describing the electrocardiogram data.

12. The system of claim 10, wherein the signal metric is selected from the list consisting of a PR interval, a QRS duration, a P axis, and a number of beats per minute.

13. A method of signal digitization, the method comprising:
- using a camera and at least a processor, capturing an image of a signal;
- using the at least a processor, determining a signal metric as a function of the image of the signal;
- using the at least a processor, generating a medical condition datum using a trained medical condition machine learning model as a function of the image, wherein generating the medical condition datum comprises selecting the medical condition machine learning model from a plurality of medical condition machine learning models as a function of a calibration datum; and
- using a user interface and the at least a processor, displaying the signal metric and the medical condition datum to a user;
- wherein the at least a processor is communicatively connected to a repository of deidentified patient health information.

14. The method of claim 13, wherein the signal comprises electrocardiogram data.

* * * * *